(12) United States Patent
Yamato et al.

(10) Patent No.: US 8,455,256 B2
(45) Date of Patent: Jun. 4, 2013

(54) SAMPLE PROCESSING APPARATUS AND SAMPLE RACK TRANSPORTING METHOD

(75) Inventors: Takashi Yamato, Kakogawa (JP); Hiroshi Kurono, Kobe (JP); Hiroki Koike, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 12/883,637

(22) Filed: Sep. 16, 2010

(65) Prior Publication Data
US 2011/0123397 A1    May 26, 2011

(30) Foreign Application Priority Data
Sep. 17, 2009 (JP) .................. 2009-215900

(51) Int. Cl.
*G01N 35/04* (2006.01)
(52) U.S. Cl.
USPC ............... 436/47; 436/50; 422/63; 422/65; 422/67

(58) Field of Classification Search
None
See application file for complete search history.

(56) References Cited

U.S. PATENT DOCUMENTS

| | | |
|---|---|---|
| 2006/0216199 A1* | 9/2006 | Koike .................. 422/65 |
| 2008/0014118 A1 | 1/2008 | Kitagawa et al. |
| 2009/0220379 A1* | 9/2009 | Wakamiya et al. ............ 422/65 |
| 2010/0248374 A1* | 9/2010 | Kitagawa et al. ............. 436/47 |

* cited by examiner

*Primary Examiner* — P. Kathryn Wright
(74) *Attorney, Agent, or Firm* — Sughrue Mion, PLLC

(57) ABSTRACT

A sample processing apparatus, including: a sample processing unit for obtaining a sample from a sample container positioned at a sample obtaining position and performing a predetermined process of the sample; a transport unit for transporting a sample rack holding the sample container via the sample obtaining position; and a transport controller for performing a stop process to stop the transport operation of the sample rack by the transport unit when a transport suspension event has occurred during the transport operation of the sample rack, and for controlling the transport unit to restart the transport operation of the sample rack from a stop position at which the sample rack has been stopped by the stop process.

17 Claims, 23 Drawing Sheets

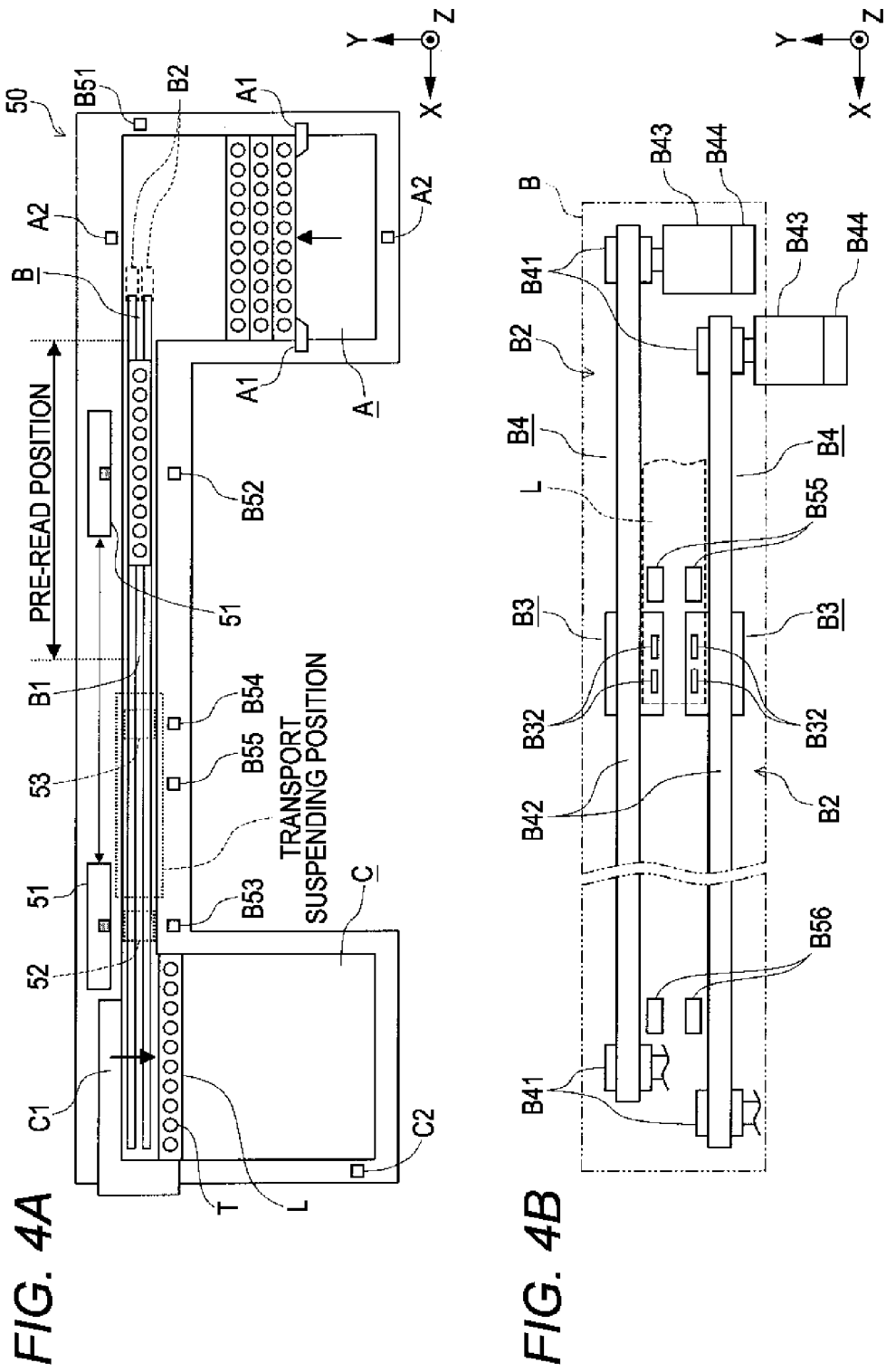

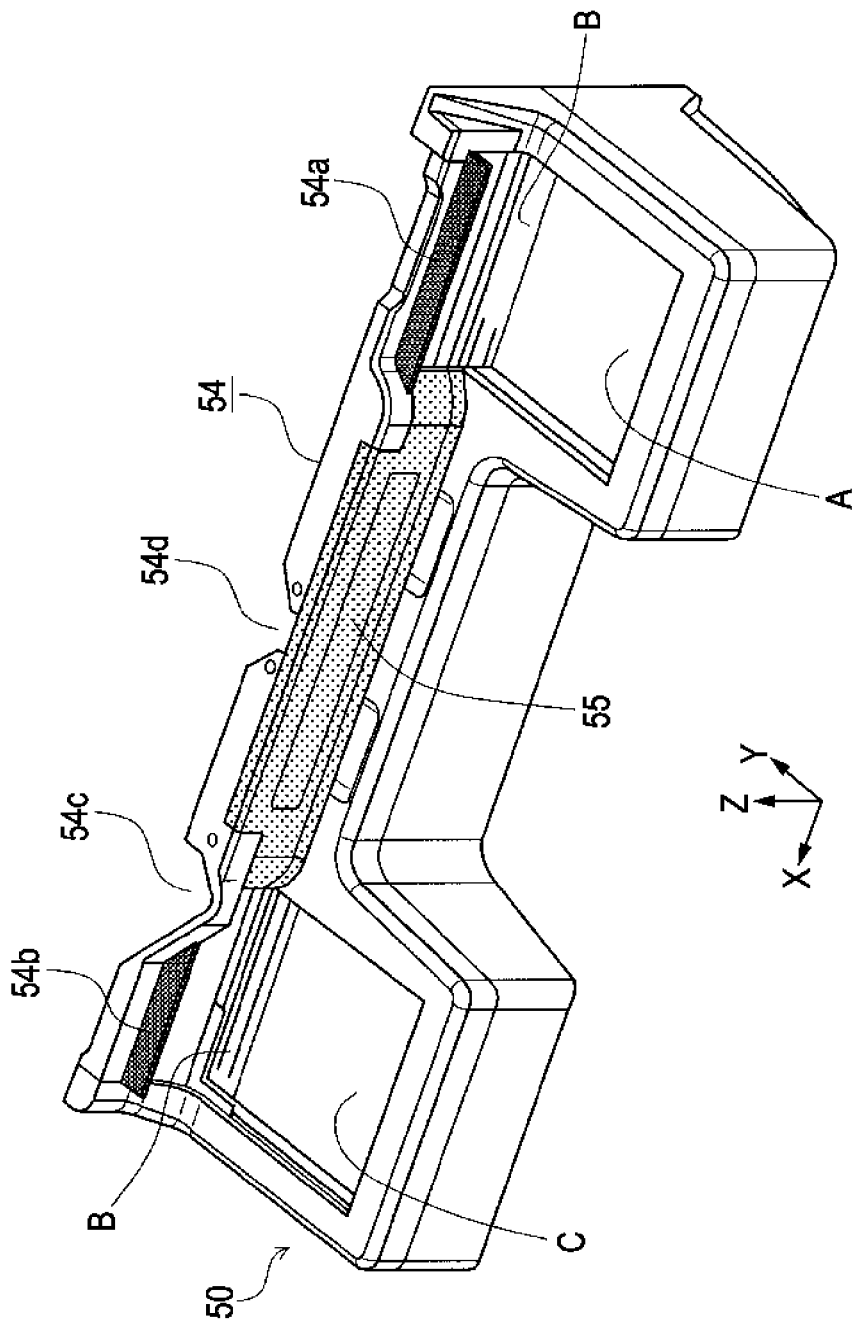

FIG. 14A

| RACK POSITION | HOLDING POSITION | SAMPLE BARCODE READ STATUS | MEASUREMENT MODE | SUCTIONING STATUS |
|---|---|---|---|---|
| SAMPLE SUCTIONING POSITION | 1 | FINISHED | STANDARD | FINISHED |
| | 2 | FINISHED | STANDARD | FINISHED |
| | 3 | FINISHED | STANDARD | FINISHED |
| | 4 | FINISHED | STANDARD | FINISHED |
| | 5 | FINISHED | TRACE LEVEL | FINISHED |
| | 6 | FINISHED | TRACE LEVEL | UNFINISHED |
| | 7 | FINISHED | STANDARD | UNFINISHED |
| | 8 | FINISHED | STANDARD | UNFINISHED |
| | 9 | FINISHED | STANDARD | UNFINISHED |
| | 10 | FINISHED | STANDARD | UNFINISHED |

FIG. 14B

| RACK POSITION | HOLDING POSITION | SAMPLE BARCODE READ STATUS | MEASUREMENT MODE | SUCTIONING STATUS |
|---|---|---|---|---|
| PRE-READ POSITION | 1 | FINISHED | STANDARD | UNFINISHED |
|  | 2 | FINISHED | STANDARD | UNFINISHED |
|  | 3 | FINISHED | STANDARD | UNFINISHED |
|  | 4 | FINISHED | TRACE LEVEL | UNFINISHED |
|  | 5 | FINISHED | TRACE LEVEL | UNFINISHED |
|  | 6 | UNFINISHED | STANDARD | UNFINISHED |
|  | 7 | UNFINISHED | TRACE LEVEL | UNFINISHED |
|  | 8 | UNFINISHED | TRACE LEVEL | UNFINISHED |
|  | 9 | UNFINISHED | STANDARD | UNFINISHED |
|  | 10 | UNFINISHED | TRACE LEVEL | UNFINISHED |

FIG. 15

| STATE | RACK NUMBER–POSITION | SAMPLE NUMBER | MEASUREMENT MODE | DATE | TIME | PT% |
|---|---|---|---|---|---|---|
| ... | ... | ... | ... | ... | ... | ... |
| | 000001–01 | 1* | N | 2009/01/05 | 13:15 | 121.3 |
| | 000001–01 | 1* | N | 2009/01/05 | 16:59 | 121.3 |
| | 000001–02 | 2* | N | 2009/01/05 | 16:59 | 102.9 |
| | 000001–03 | 3* | M | 2009/01/05 | 17:00 | 64.1 |
| | 000001–04 | 4* | M | 2009/01/05 | 17:00 | 118.8 |
| | 000001–05 | 5* | N | 2009/01/05 | 17:07 | 48.0 |
| | 000001–01 | 1* | N | 2009/01/05 | 17:07 | 10.7 |
| | 000001–02 | 2* | N | 2009/01/05 | 17:07 | 10.5 |
| ERROR | 000001–03 | 3* | N | | | *****.* |
| ERROR | 000001–04 | 4* | N | | | *****.* |

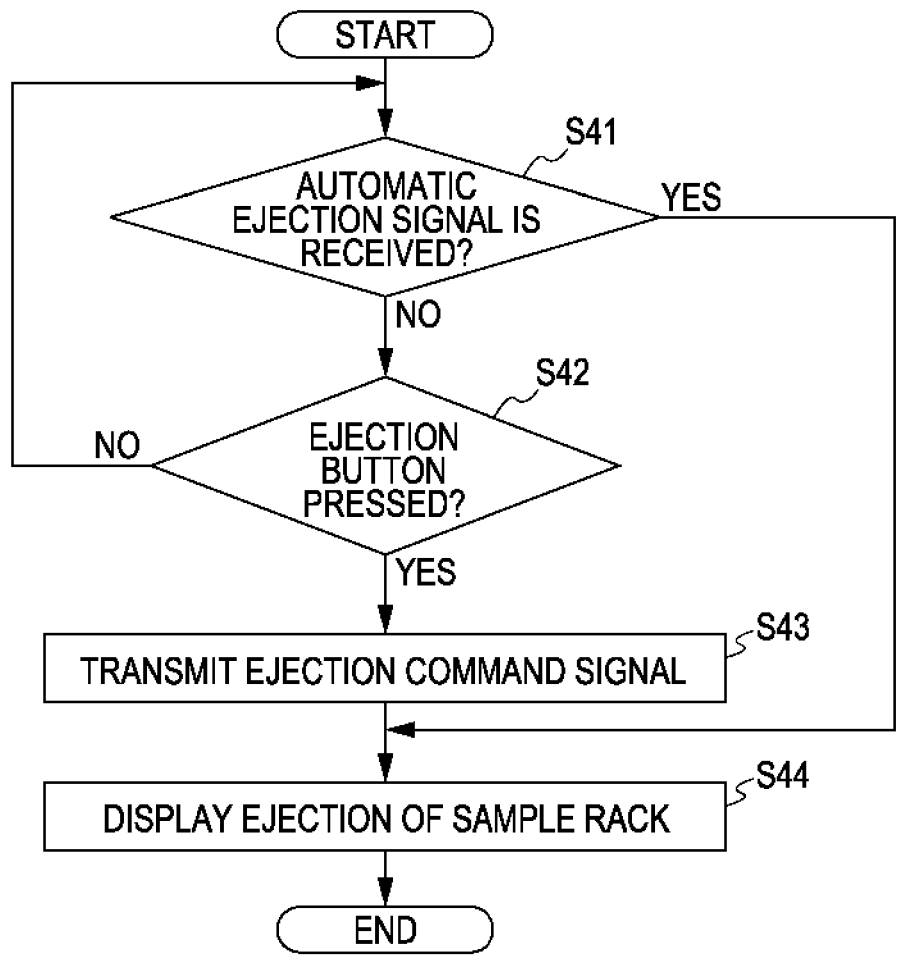

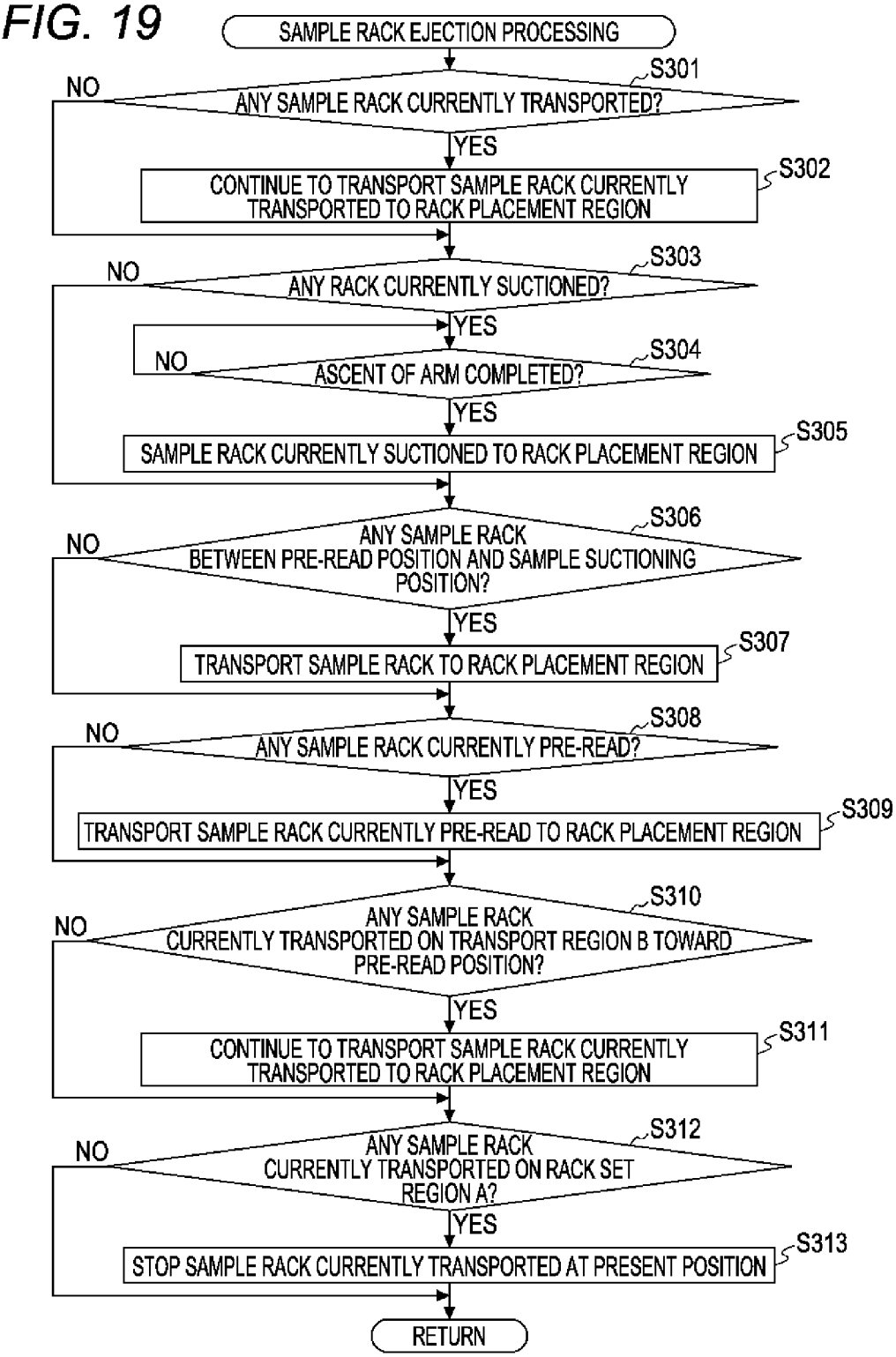

SAMPLE PROCESSING APPARATUS AND SAMPLE RACK TRANSPORTING METHOD

FIELD OF THE INVENTION

The present invention relates to a sample processing apparatus for processing a sample such as blood or urine, and a sample rack transporting method.

BACKGROUND

U.S. Patent Publication No. 2008/014118 discloses a sample processing apparatus for suctioning a sample from a sample container held by a sample rack and processing the suctioned sample. Such a sample processing apparatus is equipped with a transport device for transporting a sample rack holding sample containers to a suctioning position. The sample rack holding a plurality of sample containers is set in a rack set region on the transport device. The sample rack thus set in the rack set region is transported by the transport device toward the suctioning position in front of a measurement device so that the sample containers housed in the sample rack are one by one placed at the suctioning position. During the transport of the sample rack to the suctioning position, barcodes affixed to all of the sample containers housed in the sample rack are read by a barcode reader. After the samples in all of the sample containers housed in the sample rack are suctioned, the sample rack is transported to a rack placement region on the transport device.

Such a sample processing apparatus temporarily stops the transport operation of the sample rack when a predetermined transport suspension event has occurred during the transport operation of the sample rack. In this case, a user returns the sample rack from a position where the transport operation was suspended to the rack set region before restarting the transport operation of the sample rack.

The conventional sample processing apparatus, however, imposes an additional burden on the user because the user always has to return the sample rack to the rack set region to restart the transport operation.

SUMMARY

The scope of the present invention is defined solely by the appended claims, and is not affected to any degree by the statements within this summary.

A first aspect of the present invention is a sample processing apparatus, comprising: a sample processing unit for obtaining a sample from a sample container positioned at a sample obtaining position and performing a predetermined process of the sample; a transport unit for transporting, in a transport operation, a sample rack holding the sample container via the sample obtaining position; and a transport controller for performing a stop process to stop the transport operation of the sample rack by the transport unit after a transport suspension event occurs during the transport operation, and for controlling the transport unit to restart the transport operation from a stop position of the sample rack associated with the stop process.

A second aspect of the present invention is a sample processing apparatus, comprising: a transport unit configured to transport a plurality of samples, in racks of respective sample containers, through a transport region that includes a sample obtaining position at which the samples are each processed for analysis; and a processor electronically controlling the transportation unit to variously (a) transport the samples along a predetermined path through the transport region, (b) stop the transport in response to detection of a transport suspension event, and (c) restart the transport after detection of a transport resumption event; and a mechanism configured to positionally secure at least one of the containers and the racks in the transport region for a given time period following the stop and prior to the restart.

A third aspect of the present invention is sample rack transporting method comprising: in a transport operation, transporting a sample rack holding a sample container by a transport unit; obtaining a sample from the sample container positioned at a sample obtaining position by the transport unit and performing a predetermined process of the obtained sample; stopping a transport operation of the sample rack by the transport unit a transport suspension event occurs during the transport operation; and restarting the transport operation by the transport unit from a stop position of the sample rack stopped by the stopping of the transport operation.

BRIEF DESCRIPTION OF THE DRAWINGS

FIGS. 4A and 4B are plan views illustrating a structure of a transport unit according to the embodiment;

FIG. 6 is a perspective view of a transport unit according to the embodiment;

FIG. 14A is a diagram illustrating a transport operation control list of a preceding rack according to the embodiment, and FIG. 14B is a diagram illustrating a transport operation control list of a subsequent rack according to the embodiment;

FIG. 15 is a diagram illustrating a job list according to the embodiment;

FIGS. 18A and 18B are flowcharts illustrating an ejection processing according to the embodiment, FIG. 19 is a flowchart illustrating a sample rack ejection processing according to the embodiment.

DETAILED DESCRIPTION OF THE EMBODIMENT

Hereinafter, a sample processing apparatus according to an embodiment is described with reference to the accompanied drawings. The embodiment described below is only illustrated as an example of embodying the present invention. The present invention is by no means limited to the embodiment described below.

Figure 1:
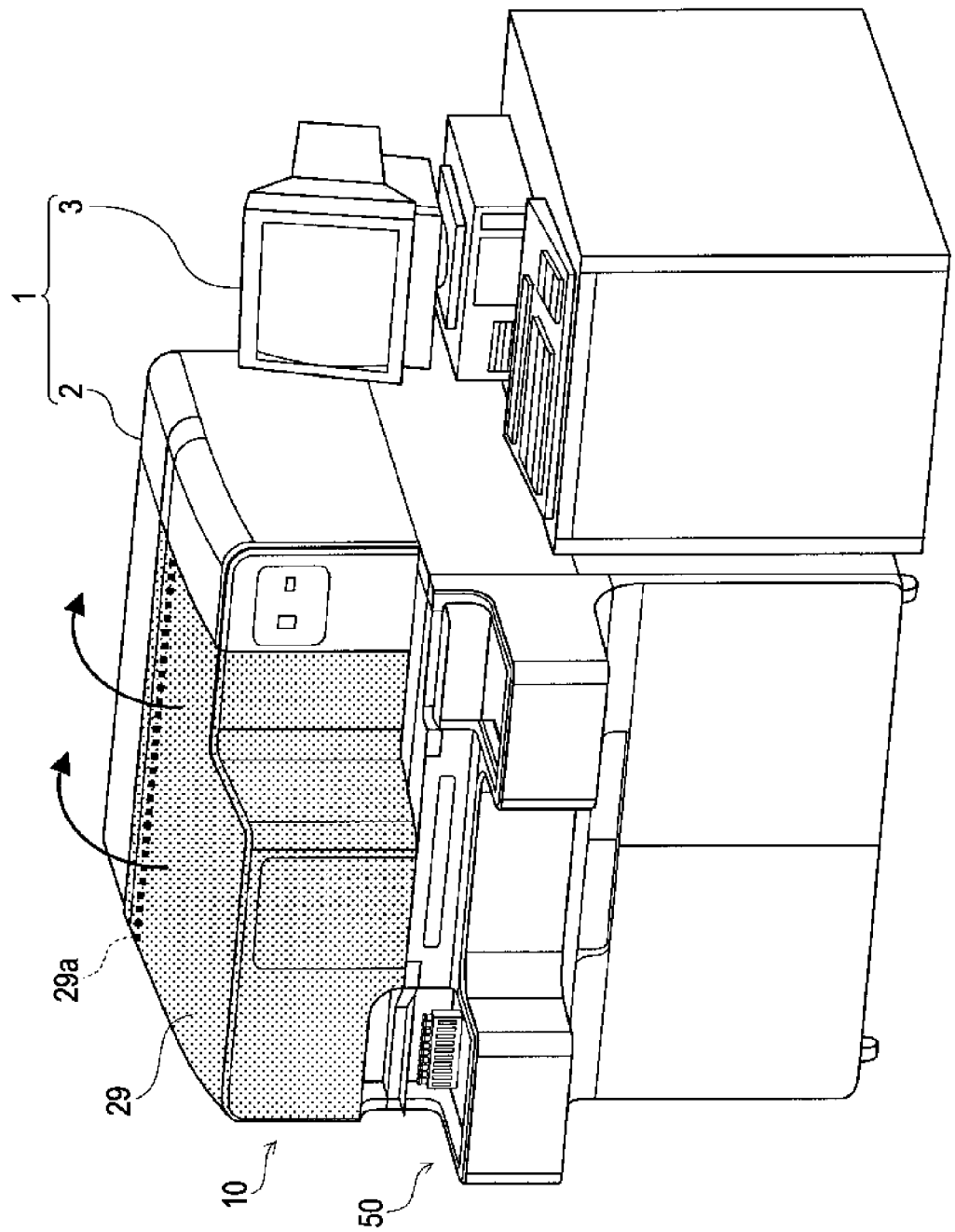
FIG. 1 is a diagram illustrating a structure of a sample processing apparatus according to an embodiment.

FIG. 1 is a diagram illustrating a structure of a sample processing apparatus 1 according to the present embodiment. The sample processing apparatus 1 is a blood coagulation analyzing apparatus for optically measuring and analyzing a sample by irradiating with light a measurement specimen prepared by adding a reagent to the sample (plasma) by employing techniques of solidification, synthetic substrate, immunonephelometry, and agglutination. The sample processing apparatus 1 has a measurement device 2 which optically measures components included in the sample (plasma), and an information processing device 3 which analyzes measurement data obtained by the measurement device 2 and transmits operation commands to the measurement device 2.

The measurement device 2 is provided with a main body cover 29 as illustrated in the figure. As the main body cover 29 rotates on a rotational shaft 29a as illustrated in the figure, a measurement unit 10 described later can be opened or closed.

Figure 2:
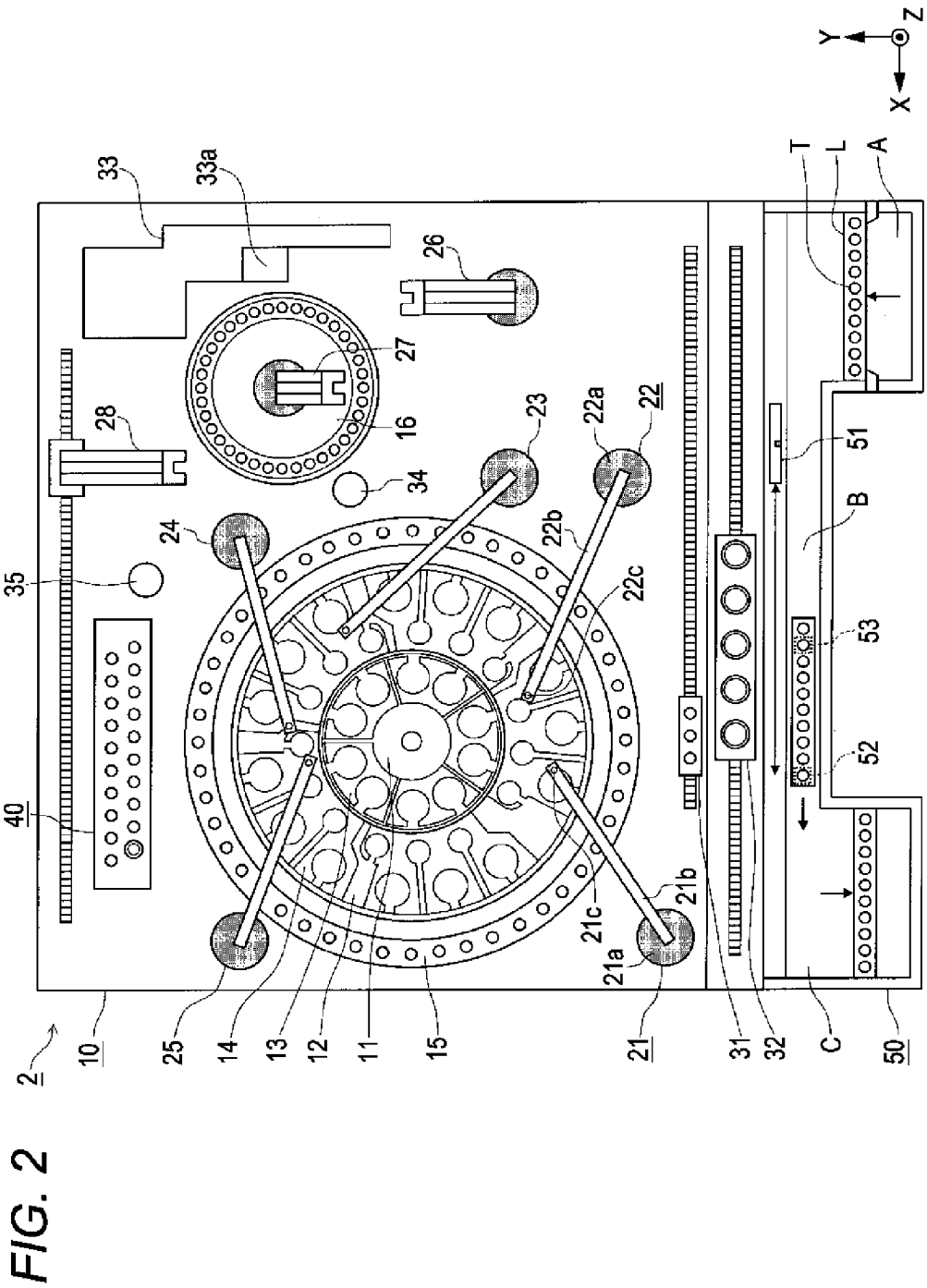
FIG. 2 is a plan view schematically illustrating an internal structure of a measurement device according to the embodiment.

FIG. 2 is a plan view schematically illustrating an internal structure of the measurement device 2 when viewed from an upper direction. The measurement device 2 includes the measurement unit 10, a detection unit 40, and a transport unit 50.

As illustrated in the figure, the transport unit 50 is provided with a rack set region A where a sample rack L can be disposed, a transport region B, and a rack placement region C. The sample rack L has holding sections so that a plurality of sample containers T can be held therein. The sample container T contains therein a sample to be measured.

The sample rack L set in the rack set region A is transported rearward along the rack set region A (Y-axis positive direction) to reach the right end of the transport region B (end in X-axis negative direction). The sample rack L positioned at the right end of the transport region B is then transported leftward (X-axis positive direction) along the transport region B.

As illustrated in the figure, a barcode reader 51, which is movable rightward and leftward (X-axis negative and positive directions), is provided in the transport region B. The barcode reader 51 reads barcode labels respectively affixed to the sample container T and the sample rack L at a predetermined position on the transport region B. Sample suctioning positions 52 and 53 are set at predetermined positions of the transport region B.

When the sample containers T are positioned at the sample suctioning positions 52 and 53, the samples contained in the sample containers T at the positions are respectively suctioned by sample dispensing units 21 and 22 described later. After all of the samples in the sample containers T held in the sample rack L are suctioned, the sample rack L is transported to the left end of the transport region B.

In the sample processing apparatus 1 according to the present embodiment, a measurement mode from two different measurement modes; "standard measurement" and "trace-level measurement" can be selected. In the standard measurement, the sample of the sample container T is suctioned by the sample dispensing unit 21 at the sample suctioning position 52. In the trace-level measurement, the sample of the sample container T is suctioned by the sample dispensing unit 22 at the sample suctioning position 53.

The sample rack L positioned at the left end of the transport region B is transported forward along the rack placement region C (Y-axis negative direction), where the transport operation of the sample rack L ends. The transport operation by the transport unit 50 is consecutively carried out for all of the sample racks L set in the rack set region A.

The sample dispensing unit 21 includes a support member 21a, an arm 21b supported by the support member 21a, and a pipette 21c attached to a tip of the arm 21b. The support member 21a is rotated by a stepping motor 211a provided on a rear side of a lower surface (see FIG. 7), and the arm 21b is driven upward and downward by the stepping motor 211a (Z-axis positive and negative directions). The pipette 21c is used to suction and discharge the sample. When the support member 21a is rotated, the pipette 21c moves on an outer periphery of a circle centered on the support member 21a.

The sample dispensing unit 22 has a structure similar to that of the sample dispensing unit 21. More specifically, the sample dispensing unit 22 includes a support member 22a, an arm 22b, and a pipette 22c attached to a tip of the arm 22b. The support member 22a is rotated by a stepping motor 211b provided on the lower-surface rear side (see FIG. 7), and the arm 22b is driven upward and downward by the stepping motor 211b. The pipette 22c is used to suction and discharge the sample.

To suction the samples, to start with, the sample dispensing units 21 and 22 respectively rotate the support members 21a and 22a to position the pipettes 21c and 22c at the sample suctioning positions 52 and 53. When the arms 21b and 22b are thereafter driven downward, the pipettes 21c and 22c are inserted into the sample containers T. After the samples are suctioned, the arms 21b and 22b are driven upward so that the pipettes 21c and 22c are drawn out of the sample containers T.

The samples suctioned at the sample suctioning positions 52 and 53 are put in cuvettes of a cuvette carrier 31 directly or by way of cuvettes of a cuvette table 15. At this time, a suitable volume of diluent set in a diluent carrier 32 is suctioned by the sample dispensing unit 22 to be mixed with the samples of the cuvettes. Then, the cuvette carrier 31 is driven rightward (X-axis negative direction) so that the cuvettes are transported to the front of a catcher unit 26. The cuvettes set in the cuvette carrier 31 are held by the catcher unit 26 and then set in a warming table 16. Then, the cuvettes are transported by catcher units 27 and 28 to be set in the detection unit 40. At this time, a suitable volume of reagents retained in reagent tables 11 and 12 are injected into the cuvettes by reagent dispensing units 23, 24 and 25. Then, the detection unit 40 processes the contents of the cuvettes to detect optical information which reflects thereon components included in the measurement specimens in the cuvettes.

A cuvette supply unit 33 can sequentially supply a plurality of cuvettes thus obtained to a cuvette storage 33a. The cuvettes newly supplied to the cuvette storage 33a are set in retaining holes of the cuvette table 15 and the cuvette carrier 31 by the catcher units 26 and 27, respectively. The post-analysis cuvettes to be discarded are thrown into waste vents 34 and 35 by the catcher units 27 and 28. The sample dispensing units 21 and 22, and the pipettes of the reagent dispensing unit 23 to 25 are washed at a predetermined washing position (not illustrated). A washing solution which was used for washing is kept in a waste solution tank (not illustrated).

On the reagent tables 11 and 12, container racks 13 and 14 are respectively disposed. The container racks 13 and 14 respectively hold therein a plurality of reagent containers in which reagents are contained. To exchange the reagents contained in the reagent container, the main body cover 29 illustrated in FIG. 1 is opened after the measuring operation by the measurement unit 10 is suspended. Then, an operator can retrieve the reagent containers from the reagent tables 11 and 12 to replace the reagents with new ones.

Figure 3A:
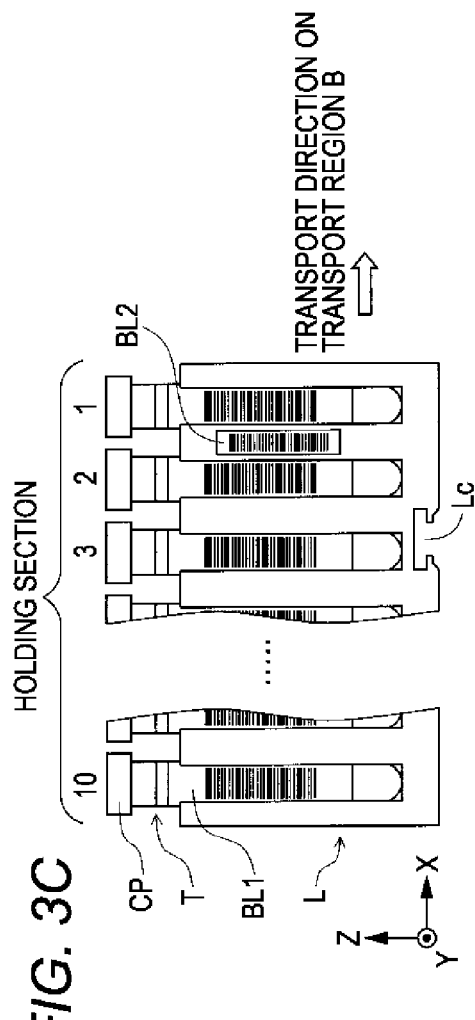
FIG. 3A is a diagram of a sample container according to the embodiment.
Figure 3B:
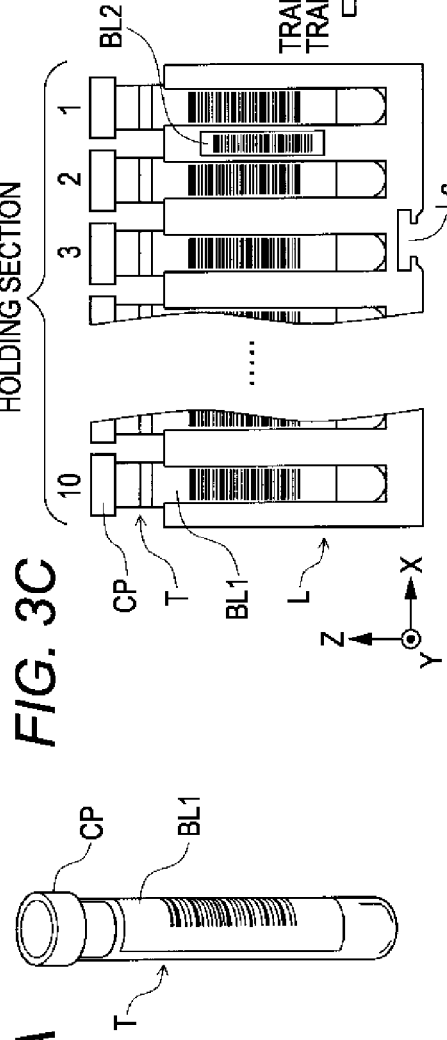
FIGS. 3B and 3C are diagrams illustrating a structure of a sample rack according to the embodiment.
Figure 3C:
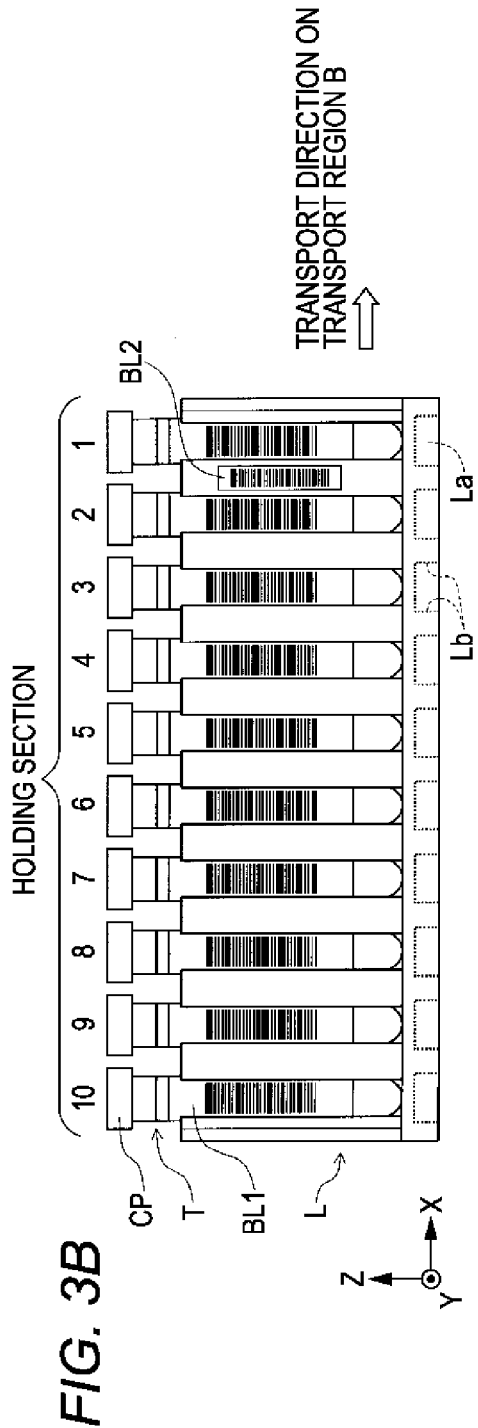

FIG. 3A is a perspective view illustrating an external appearance of the sample container T, and FIGS. 3B and 3C are front views of the sample rack L. FIG. 3B and FIG. 3C are front views of the sample rack L when the sample rack L set in the transport unit 50 is viewed in the Y-axis negative direction illustrated in FIG. 2.

Referring to FIG. 3A, the sample container T is a tubular container made of optically transparent glass or synthetic resin, wherein an upper end is open. A blood sample collected from a patient is contained therein, and the opening at the upper end thereof is sealed with a cap portion CP. A barcode label BL1 is affixed to a side surface of the sample container T. The barcode label BL1 has a barcode representing a sample ID printed thereon.

Referring to FIG. 3B, the sample rack L has 10 holding sections which can hold 10 sample containers T perpendicularly (upright position). The holding sections respectively have serial numbers 1 to 10 from right which represent their holding positions. A barcode label BL2 is affixed to a side surface of the sample rack L in the Y-axis positive direction. The barcode label BL2 has a barcode representing a rack ID printed thereon.

As illustrated in FIG. 3B, recesses La as many as the holding sections, that is, 10 recesses open downward are formed in a bottom surface of the sample rack L along the longitudinal direction of the sample rack L. The recesses La are each defined by wall portions Lb formed on right and left sides thereof.

The sample rack may have a structure as illustrated in FIG. 3C. In this case, a bottom surface of the sample rack L is provided with one recess Lc.

FIG. 4A is a plan view illustrating a structure of the transport unit 50.

The rack set region A is equipped with a rack feed mechanism A1 which transports the sample rack L disposed therein in the Y-axis positive direction. The rack feed mechanism A1 pushes the side surface of the sample rack L in the rack set region A closer thereto (in Y-axis negative direction) to transport the sample rack L in the Y-axis positive direction so that the sample rack L is transferred to the transport region B. In the event that a plurality of sample racks L are disposed in the rack set region A, as illustrated in the figure, the rack feed mechanism A similarly pushes the side surface of the sample rack L which is nearest thereto (in Y-axis negative direction) so that the sample rack L which is farthest thereto (in Y-axis positive direction) is transferred to the transport region B.

In the rack set region A, as illustrated in the figure, a pair of sensors A2 are provided at an end thereof in the Y-axis positive direction and an end thereof in the Y-axis negative direction. An optically transparent photosensor or the like constitutes the sensor A2. The sensor A2 blocks light when the sample rack L is present in the rack set region A, and transmits light when there is no sample rack L in the rack set region A.

The transport region B is provided with a transport path B1 which supports the bottom surface of the sample rack L, and two rack transverse feed mechanisms B2. The two rack transverse feed mechanisms B2 are provided below the transport path B1, and independently move two sample racks L disposed on the transport path B1 rightward and leftward (X-axis positive and negative directions). A structure of the rack transverse feed mechanism B2 will be described later with reference to FIG. 4B and FIG. 5.

In the sample rack L transferred to the transport region B, the barcode reader 51 reads the barcode BL1 of the sample container T and the barcode label BL2 of the sample rack L (hereinafter, referred to as "pre-read") before the sample container T is transported to the sample suctioning position 52, 53. As illustrated in the figure, the pre-read by the barcode reader 51 is performed when the sample rack L is in the range of "a pre-read position" on the transport region B.

As illustrated in FIG. 2, the sample suctioning positions 52 and 53 are set in the transport region B. The sample rack L for which the pre-read was performed is transported leftward (X-axis positive direction) so that the sample containers T retained in the sample rack L is positioned at the sample suctioning position 52 or 53. The barcode label BL1 of the sample container T positioned at the sample suctioning position 52 or 53 is read by the barcode reader 51 (hereinafter, referred to as "post-read"), and the sample contained therein is then suctioned.

If a transport suspension event, which will be described later, occurs when the sample suctioning by the sample dispensing units 21 and 22 is currently performed, the sample rack L is transferred to "a transport suspending position" and stops there.

As illustrated in the figure, sensors B51 to B55 are provided in the transport region B. A reflective photosensor or the like constitutes each of the sensors B51 to B55. The sensor B51 detects the sample rack L positioned at the right end of the transport region B (end in the X-axis negative direction). The sensor B52 detects that the sample rack L has been transported to the pre-read position. The sensors B53 and B54 detect that the sample rack L is positioned at the sample suctioning position 52, 53. The sensor B55 detects that the sample rack L has been transported to the transport suspending position.

The rack placement region C is provided with a rack feed mechanism C1 which transports the sample rack L disposed therein in the Y-axis negative direction. The rack feed mechanism C1 moves the sample rack L disposed at the left end of the transport region B (end in the X-axis positive direction) in the Y-axis negative direction by one pitch (equal to width of the sample rack L in its lateral direction) so that the sample rack L is transferred from the transport region B to the rack placement region C.

As illustrated in the figure, the rack placement region C is equipped with a sensor C2 which detects the presence or absence of the sample rack L. A reflective photosensor or the like constitutes the sensor C2. The sensor C2 detects the sample rack L which has been transported to a transport end position (end in the Y-axis negative direction) of the rack placement region C.

FIG. 4B is a plan view illustrating a structure of the rack transverse feed mechanism B2. The two rack transverse feed mechanisms B2 are provided next to each other in the Y-axis direction. The rack transverse feed mechanism B2 is equipped with an engagement unit B3 that can be engaged with the sample rack L, and a movement mechanism B4 which moves the engagement unit B3 rightward and leftward (X-axis positive and negative directions).

The movement mechanism B4 has a pair of pulleys B41 provided at both ends of the transport region B, a belt 42 that bridges the pulleys B41, a stepping motor B43 which rotates one of the pulleys B41, and a rotary encoder B44 which detects number of rotations of the stepping motor B43.

The engagement unit B3 is coupled with the belt B42 of the movement mechanism B4 to move rightward and leftward when the stepping motor B43 is driven. An amount of the movement of the engagement unit B3 is detected by the rotary encoder B44 as the number of rotations of the stepping motor B43. The operation of the stepping motor B43 is controlled based on a detection result obtained by the rotary encoder B44. A movement start position and a movement end position of the engagement unit B3 are respectively set at a right end (end in X-axis negative direction) and a left end (end in X-axis positive direction) in a drivable range of the engagement unit B3. Further, sensors B55 and B56 each including an optically transparent photosensor or the like are provided. The sensors B55 and B56 respectively detect the engagement unit B3 positioned at the movement start position and the movement end position.

Figure 5A:
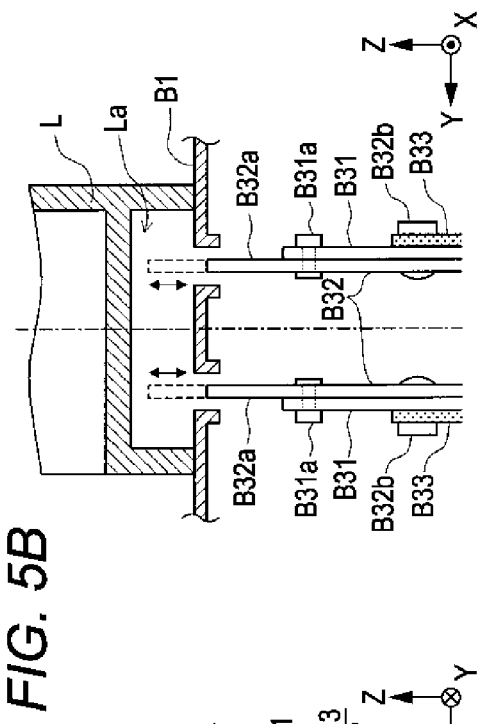
FIGS. 5A to 5D are schematic diagrams illustrating principal parts of an engagement unit according to the embodiment.
Figure 5B:
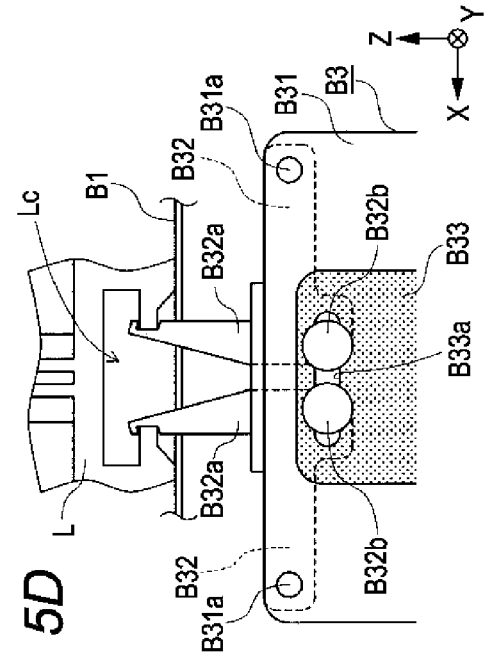
Figure 5C:
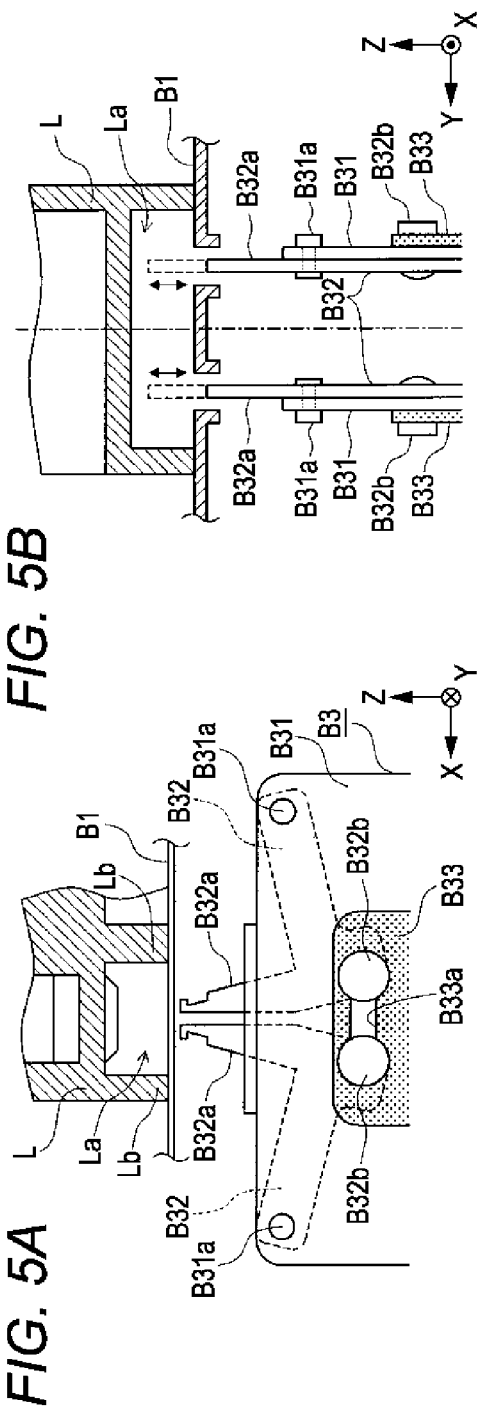
Figure 5D:
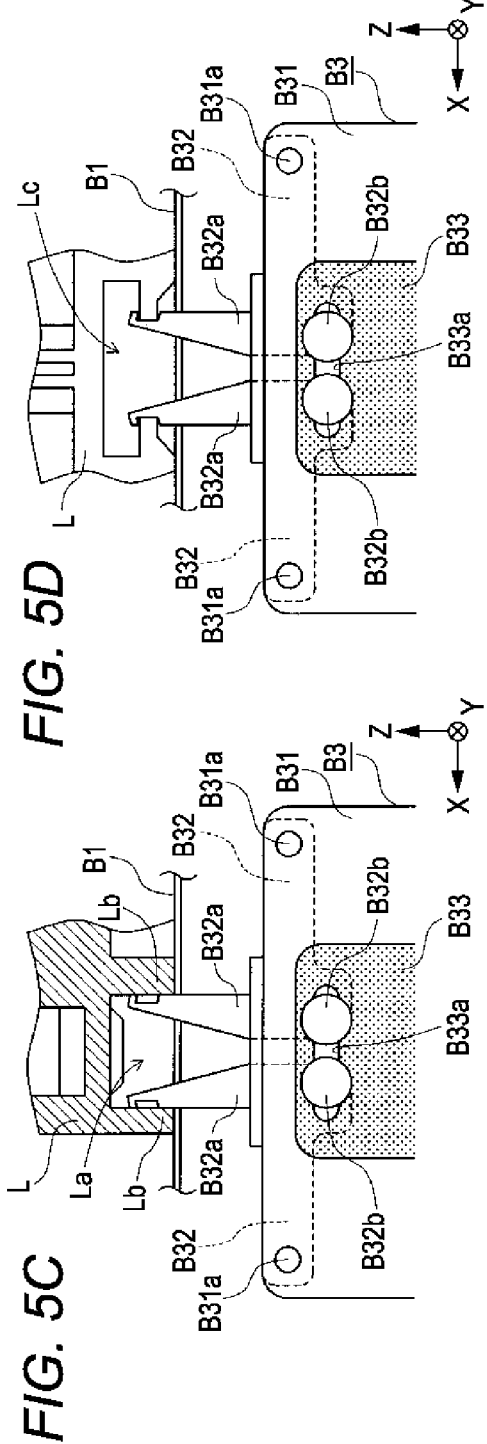

FIG. 5A is a front view of the engagement units B3 illustrating a state where the engagement units B3 are not engaged with the sample rack L. FIG. 5B is a side view of the engagement units B3. FIGS. 5C and 5D are front views of the engagement units B3 illustrating a state where the engagement units B3 are engaged with the sample rack L.

Referring to FIG. 5A, the engagement unit B3 has a substrate B31, a pair of engagement members B32, and an action member B33. The engagement unit B3 further has an air cylinder B34 (not illustrated), which moves the action member B33 upward and downward (see FIG. 7).

A guide member (not illustrated) is attached to the substrate B31. The guide member is slidably engaged with a guide rail (not illustrated) along the X-axis direction below the transport path B1. The substrate B31 is supported by the guide rail so as to freely move in the X-axis positive and negative directions.

As illustrated in the figure, the pair of engagement members B32 are secured to an upper side of the substrate B31 by securing tools B31a including bolts and screw nuts so as to freely rotate in the Y-axis direction. Engagement claws B32a are formed at an upper section of the engagement member B32, and engagement rollers B32b are provided at a lower end thereof. The substrate B31 has regulating holes (not illustrated) formed therein each regulating a rotational range of the engagement roller B32b along a rotational line of the engagement roller B32b when the engagement member B32 rotates on the securing tool B31a as a rotational center. The engagement roller 32b is movably engaged with the regulating hole. Accordingly, the engagement member B32 can be rotated in the Y-axis direction within a predetermined range with the securing tool B31a as a rotational center.

A rectangular engagement hole B33a having a larger dimension in its lateral direction is formed at an upper section of the action member B33 so that the pair of engagement rollers B32b are engaged therewith. When the action member B33 is driven in the Z-axis direction, the pair of engagement members B32 respectively rotate on the securing tools B31a in the Y-axis direction via the engagement rollers 32b engaged with the engagement hole B33a. As illustrated in FIG. 5A, in a state where the pair of engagement members B32b rotate downward (Z-axis negative direction), the engagement claws B32a are positioned below the transport path B1, and does not engage with the sample rack L.

The air cylinder B34 is supplied with compressed air from a compressor (not illustrated). The air cylinder B34 has a rod which generates an up-and-down movement as the compressed air is supplied. The action member B33 is fixed to an upper end of the rod of the air cylinder B34. As the rod of the air cylinder B34 moves upward and downward, the action member B33 simultaneously moves upward and downward. In conjunction therewith, the pair of engagement members B32 rotate upward and downward.

Referring to FIG. 5B, as described above, a state where the engagement claws B32a stick out beyond the transport path B1 through grooves formed therein, and a state where the engagement claws B32a stay below the transport path B1 occur in turns as the engagement members B32 rotate, as illustrated in the figure.

Referring to FIG. 5C, when the engagement member B32 rotates upward (Z-axis positive direction), the engagement claws B32a stick out beyond the transport path B1 to advance into the recess La formed in the bottom section of the sample rack L. As a result, the pair of engagement claws B32a are moved away from each other. Accordingly, the engagement claws B32a abut with the wall portions Lb on both sides of the recess La in the X-axis positive and negative directions as illustrated in the figure. Accordingly, the pair of engagement members B32 are finally engaged with the sample rack so that the sample rack L can be securely transported.

Referring to FIG. 5D, in the case where the sample rack L illustrated in FIG. 3C is used, the engagement claws B32a similarly stick out beyond the transport path B1 to advance into the recess Lc formed in the bottom section of the sample rack L so that the pair of engagement claws B32a are moved away from each other. In this case, the engagement claws B32a are engaged with protruding wall portions formed in the recess Lc as illustrated in the figure. Accordingly, the sample rack L illustrated in FIG. 3C can be transported in the same manner as the sample rack L illustrated in FIG. 3B.

The engagement units B3 each having the structure described so far are disposed facing each other in the Y-axis direction below the transport path B1 as illustrated in FIG. 4B, so that two sample racks L is independently driven in the transport region B.

The rack transverse feed mechanism B2 having the structure and function described so far transports the sample rack L on the transport path B1 while supporting the recess La in the bottom surface of the sample rack L using the engagement claws B32a. At the time of occurrence of a transport suspension event, which will be described later, the sample rack L is stopped on the transport region B. Nevertheless, the recess La in the bottom surface of the sample rack L still remains supported by the engagement claws B32a. The stepping motor B43 is continuously excited after the sample rack L is thus stopped, which prevents any positional shift of the sample rack L.

FIG. 6 is a perspective view of the transport unit 50.

A roof 54 is provided in an upper section (Z-axis positive direction) near the center of the transport region B. At the right end of the roof 54 (end in the X-axis negative direction) and the left end of the roof 54 (end in the X-axis positive direction), flange portions 54a and 54b are respectively formed as illustrated in the figure. Further, openings 54c and 54d are formed in the roof 54 as illustrated in the figure. The sample dispensing units 21 and 22 respectively suction the samples of the sample containers T positioned at the sample suctioning positions 52 and 53 through the openings 54c and 54d. As illustrated in the figure, a front cover 55 is removably fitted on the near side of the transport region B (Y-axis negative direction).

According to the transport operation unit 50 structured as described above, upper sides of the sample rack L and the sample container T in the transport region B are left unexposed except for the areas of the openings 54a and 54b. With this structure, foreign matters are prevented from entering the sample container T in the transport region B from an upper direction, and the operator is also prevented from accidentally coming into contact with the sample rack L and the sample container T. When the transport operation unit 50 is structured as described above, the operator is prevented from coming into contact with the sample rack L and the sample container T near the center of the transport region B (area covered with the front cover 55). Thus, the operator is prevented from accidentally coming into contact with the sample rack L and the sample container T.

The pre-read position illustrated in FIG. 4 is included in the area covered with the front cover 55. Therefore, when the sample rack L is positioned at the pre-read position, the sample rack L is entirely covered with the front cover 55. The transport suspending position illustrated in FIG. 4 is also included in the area covered with the front cover 55. That is, in the case where the left end of the sample rack L sticks out of the front cover 55 when the sample of the sample rack L is suctioned, the sample rack L is positioned at the transport suspending position under the front cover 55 at the time of occurrence of a transport suspension event described later. Accordingly, the operator may be further prevented from coming into contact with the sample rack L and the sample container T during the suspension of the measuring operation.

Figure 7:
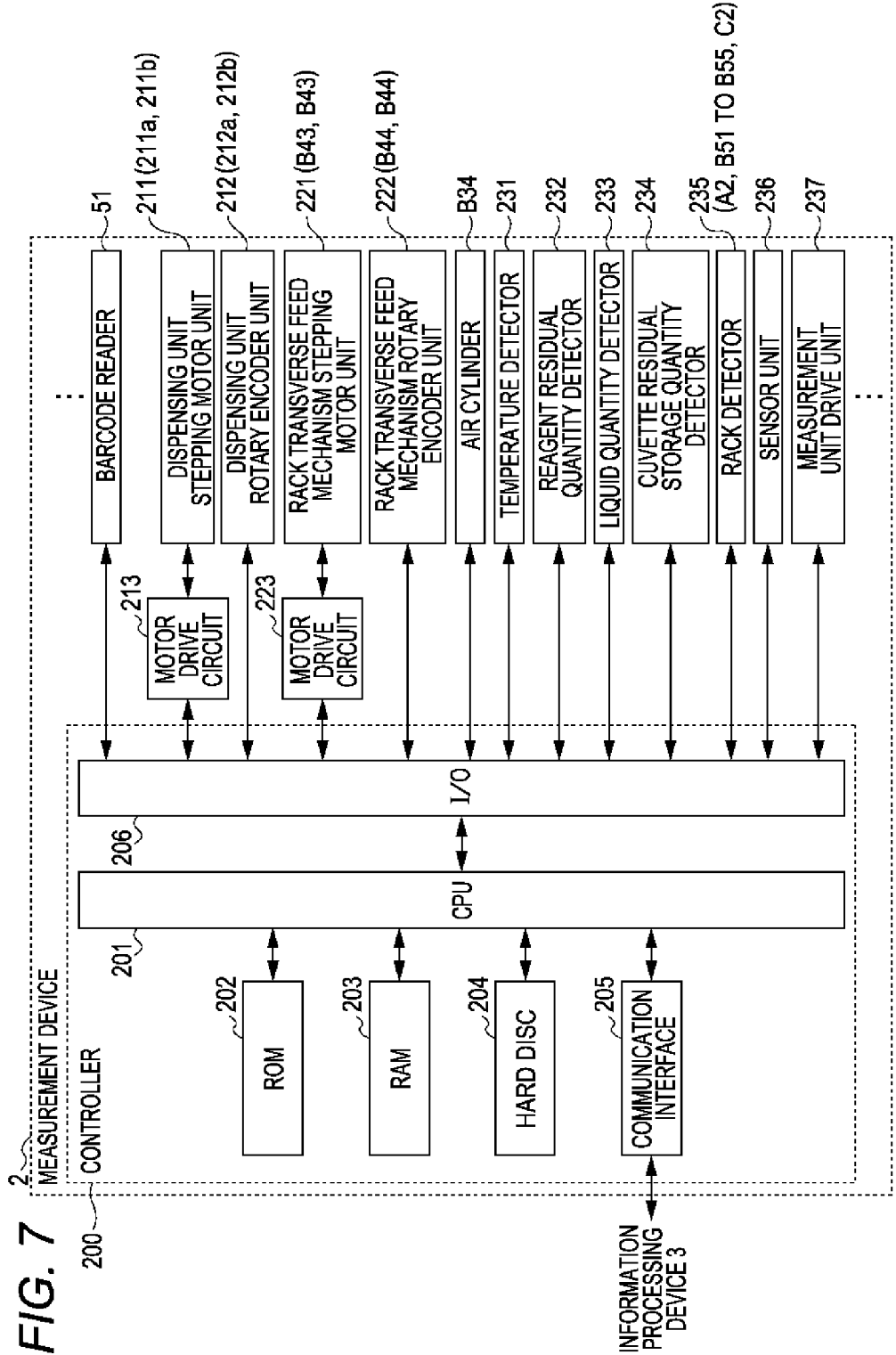
FIG. 7 is a diagram illustrating a circuit configuration of the measurement device according to the embodiment.

FIG. 7 is a diagram illustrating a circuit configuration of the measurement device 2.

The measurement device 2 includes a controller 200, a barcode reader 51, a dispensing unit stepping motor unit 211, a dispensing unit rotary encoder unit 212, a motor drive circuit 213, a rack transverse feed mechanism stepping motor unit 221, a rack transverse feed mechanism rotary encoder unit 222, a motor drive circuit 223, an air cylinder B34, a temperature detector 231, a reagent residual quantity detector 232, a liquid quantity detector 233, a cuvette storage quantity detector 234, a rack detector 235, a sensor unit 236, and a measurement unit drive unit 237.

The controller 200 includes a CPU 201, a ROM 202, a RAM 203, a hard disc 204, a communication interface 205, and an I/O interface 206.

The CPU 201 runs a computer program stored in the ROM 202 and a computer program loaded in the RAM 203. The RAM 203 is used to read computer programs recorded in the ROM 202 and the hard disc 204. The RAM 203 is also used as a working region of the CPU 201 when these computer programs are run. The hard disc 204 stores therein various computer programs to be run by the CPU 201, for example, an operating system and an application program, and data used to run these computer programs. Through the communication interface 205, data can be transmitted and received to and from the information processing device 3.

The CPU 201 is connected via the I/O interface 206 to the barcode reader 51, dispensing unit rotary encoder unit 212, motor drive circuit 213, rack transverse feed mechanism rotary encoder unit 222, motor drive circuit 223, air cylinder B34, temperature detector 231, reagent residual quantity detector 232, liquid quantity detector 233, cuvette storage quantity detector 234, rack detector 235, sensor unit 236, and measurement unit drive unit 237.

The dispensing unit stepping motor unit 211 includes stepping motors 211a and 211b which independently rotate the support member 21a of the sample dispensing unit 21 and the support member 22a of the sample dispensing unit 22. The dispensing unit rotary encoder unit 212 includes rotary encoders 212a and 212b provided for the stepping motors 211a and 211b of the sample dispensing units 21 and 22. The motor drive circuit 213 is controlled by the CPU 201 to drive the stepping motors 211a and 211b included in the dispensing unit stepping motor unit 211.

The rack transverse feed mechanism stepping motor unit 221 includes the stepping motors B43 of the two rack transverse feed mechanisms B2. The rack transverse feed mechanism rotary encoder unit 222 includes the rotary encoders B44 of the two rack transverse feed mechanisms B2. The motor drive circuit 223 is controlled by the CPU 201 to independently drive the two stepping motors B43 included in the rack transverse feed mechanism stepping motor unit 221.

The rotary encoders constituting the dispensing unit rotary encoder unit 212 and the rack transverse feed mechanism rotary encoder unit 222 are incremental encoders. The rotary encoder is configured to output a pulse signal depending on a rotational displacement of the stepping motor. The rotational speed of the stepping motor can be detected by counting the number of pulses outputted from the rotary encoder.

The temperature detector 231 is provided with a temperature sensor to detect a temperature of the warming table 16. The reagent residual quantity detector 232 is provided with a liquid surface detecting sensor to detect respective residual quantities of the reagents in the reagent containers disposed on the reagent table 11, 12. The liquid quantity detector 233 is equipped with a plurality of liquid surface detecting sensors to detect a residual quantity of the washing solution tank containing the washing solution used to wash the sample dispensing units 21 and 22 and the reagent dispensing units 23 to 25, and a waste liquid quantity of the waste washing solution tank containing the wasted solution. The cuvette storage quantity detector 234 is equipped with a cuvette storage sensor to detect a residual storage quantity of the cuvettes housed in the cuvette supply unit 33. The rack detector 235 includes sensors A2, B51 to B55 and C2 provided in the transport unit 50. The sensor unit 236 includes a photosensor which detects that the main body cover 29 is open. To carry out dispensing operations by the sample dispensing units 21 and 22 and the reagent dispensing units 23 to 25, the measurement unit drive unit 237 includes a pneumatic source for supplying pressure to these dispensing units, and a driver for driving the tables (reagent tables 11 and 12, cuvette table 15, and warming table 16).

Figure 8:
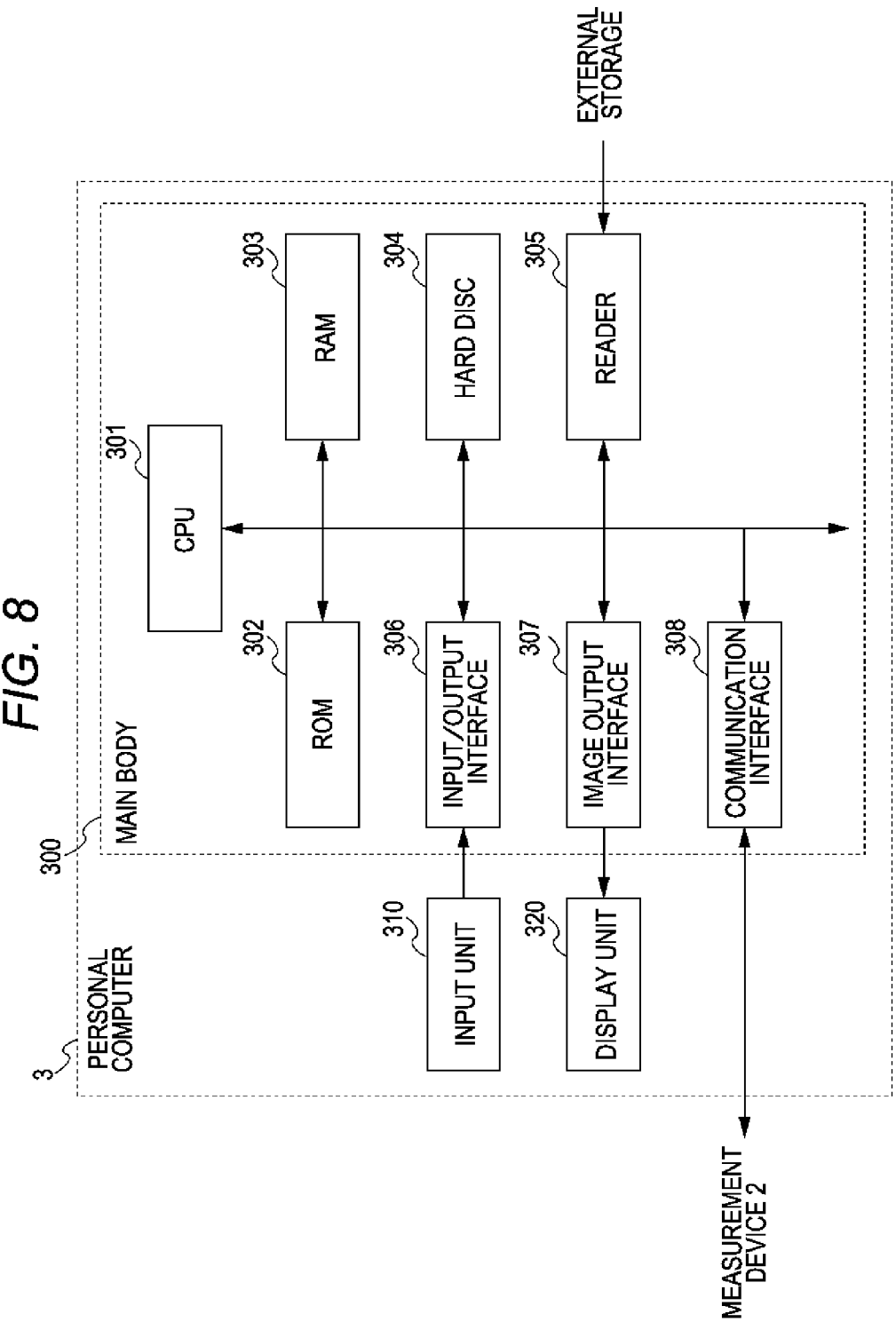
FIG. 8 is a diagram illustrating a circuit configuration of an information processing device according to the embodiment.

FIG. 8 is a diagram illustrating a circuit configuration of the information processing device 3.

The information processing device 3 includes a personal computer and also includes a main body 300, an input unit 310, and a display unit 320. The main body 300 includes a CPU 301, a ROM 302, a RAM 303, a hard disc 304, a readout device 305, an input/output interface 306, an image output interface 307, and a communication interface 308.

The CPU 301 runs a computer program stored in the ROM 302 and a computer program loaded in the RAM 303. The RAM 303 is used to read computer programs recorded in the ROM 302 and the hard disc 304. The RAM 303 is also used as a working region of the CPU 301 when these computer programs are run.

The hard disc 304 stores therein various computer programs to be run by the CPU 301, for example, an operating system and an application program, and data used to run these computer programs. Specifically, in the hard disc 304, there are installed a display program for receiving a reagent condition in the measurement device 2 to, for example, display a message notifying the reagent residual quantity on the display unit 309, and operation programs for replacing the reagent or operating the measurement device 2 in accordance with additional operation commands.

The readout device 305 includes, for example, a CD drive or a DVD drive. The readout device 305 can read computer programs and data recorded on a recording medium. The input unit 310 including a mouse and a keyboard is connected to the input/output interface 306. The operator inputs data to the information processing device 3 by using the input unit 310. The image output interface 307 is connected to the display unit 320 including, for example, a display screen to output a video signal suitable for image data to the display unit 320. The display unit 320 displays an image based on the inputted video signal. Through the communication interface 308, data can be transmitted and received to and from the measurement device 2.

Figure 9:
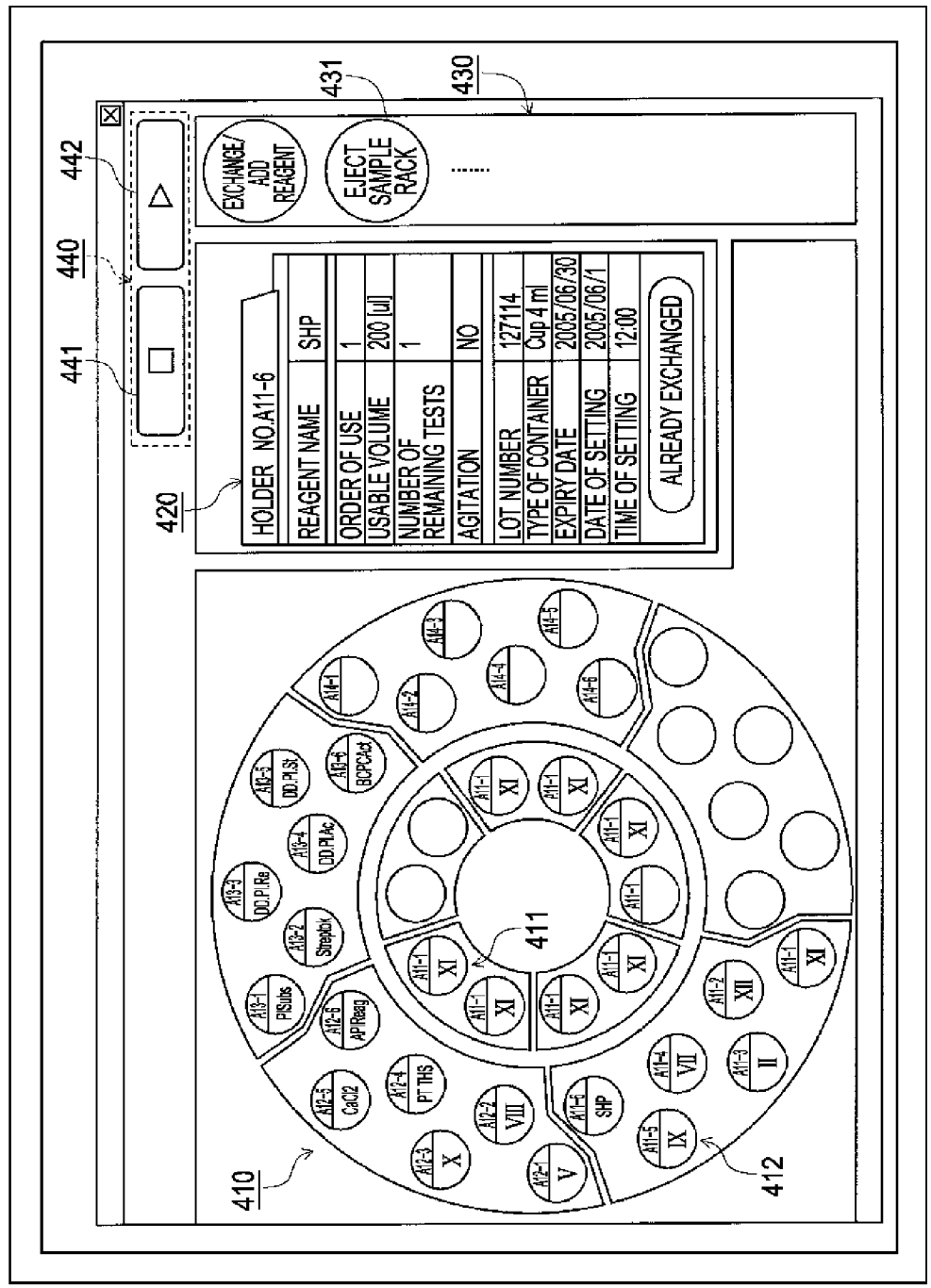
FIG. 9 is a diagram illustrating an example of a reagent information screen displayed on a display unit of the information processing device according to the embodiment.

FIG. 9 is a diagram illustrating an example of a reagent information screen displayed on the display unit 320 of the information processing device 3. The reagent information screen includes a location display region 410, a detailed information display region 420, an operation command display region 430, and an operation decision display region 440.

The location display region 410 displays the positions of the container racks 13 and 14 on the reagent tables 11 and 12, and a condition of the reagent containers housed in these container racks.

When a reagent mark 411 or 412 in the location display region 410 is selected, detailed information on contents of the reagent container retained at the position of the selected mark is displayed in the detailed information display region 420.

The operation command display region 430 has a plurality of different command buttons including a sample rack ejection button 431. When the operator presses any of the buttons, an operation corresponding to the pressed button is carried out.

The measurement command display region 440 has a measurement suspending button 441 and a measurement start button 442. When the operator presses the measurement suspending button 441, a measurement suspension processing is carried out. When the operator presses the measurement start button 442 during the suspension of the measurement, a measurement restart processing is carried out. The measurement start button 442 is displayed in active state as far as the measurement can restart. When the measurement start button 442 is pressed whenever the measurement restart is infeasible, a message is displayed on the screen so that the operator is notified of the failure to restart the measurement.

Next, the processing operation of the sample processing apparatus is described. The following processing operation, which is controlled by the information processing device 3, is carried out through data communicated between the measurement device 2 and the information processing device 3.

Figure 10:
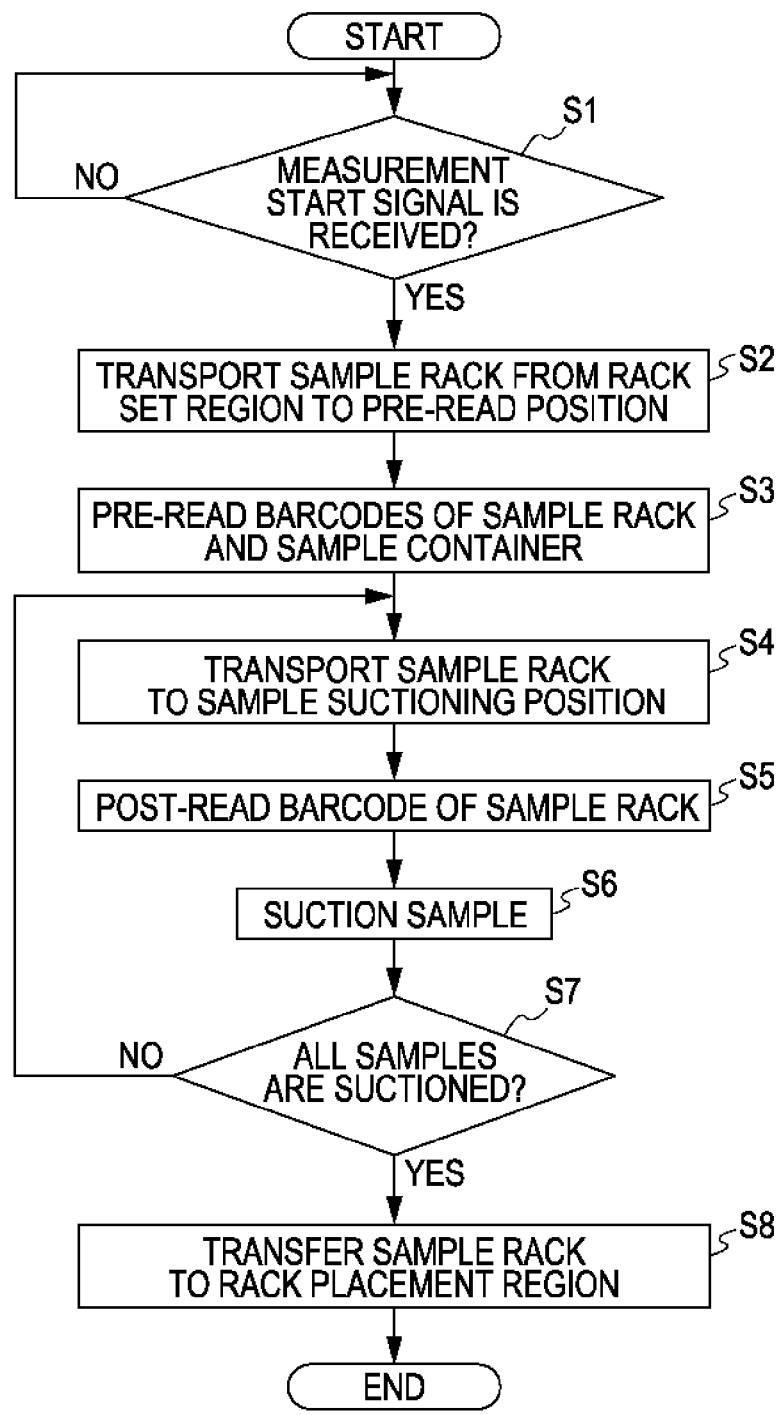
FIG. 10 is a flowchart illustrating a sample suction processing according to the embodiment.

FIG. 10 is a flowchart illustrating steps of a sample suctioning processing according to the present embodiment. In the processing flow described below, the transport position of the sample rack L is known from the output of the rack transverse feed mechanism rotary encoder unit 222 and the output of the rack detector 235.

In the present embodiment, when the operator inputs a measurement start command via the information processing device 3, the measurement device 2 starts its measuring operation. When the CPU 201 of the measurement device 2 receives a measurement start signal from the information processing device 3 (S1: YES), the CPU 201 transports the sample rack L from the rack set region A to the pre-read position (S2). At the pre-read position, the barcode reader 51 performs the pre-read of the barcode label BL2 of the sample rack L and the barcode label BL1 of the sample container T held in the sample rack L (S3).

The sample rack L, for which the barcode pre-read at the pre-read position is completed, is transported to the sample suctioning position 52 or 53 (S4). When the sample container T is positioned at the sample suctioning position 52 or 53, the barcode reader 51 performs the post-read of the barcode label BL1 affixed to the sample container T (S5). The sample of the barcode-read sample container T is suctioned by the sample dispensing unit 21 or 22 at the sample suctioning position 52 or 53 (S6).

After the samples in all of the sample containers T held in the sample rack L are suctioned (S7: YES), the sample rack L is transported to the rack placement region C (S8), and the sample suctioning processing for the sample rack L ends. Unless the samples in all of the sample containers T held in the sample rack L are suctioned (S7: NO), steps S4 to S6 are repeatedly carried out until the samples in all of the sample containers T held in the sample rack L are suctioned.

In the case where there is a subsequent sample rack L that follows the sample rack L currently positioned at the sample suctioning position 52 or 53, the processing steps in S2 and after S2 start for the subsequent sample rack L. In this case, the barcode reader 51 is moved in the X-axis positive and negative directions to post-read the preceding sample rack L with a higher priority but pre-read the subsequent sample rack L as well.

Figure 11A:
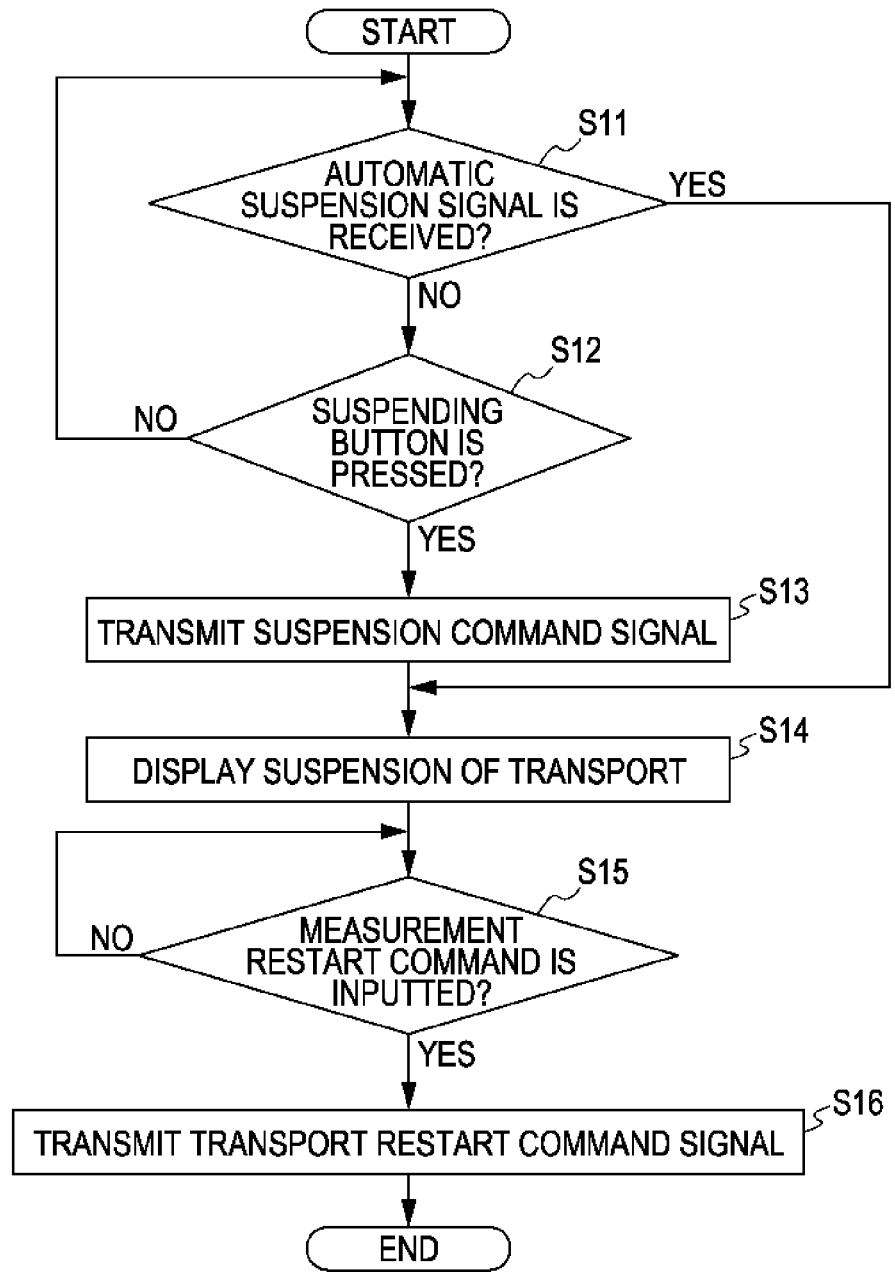
FIGS. 11A and 11B are flowcharts illustrating a suspension and restart processing according to the embodiment.
Figure 11B:
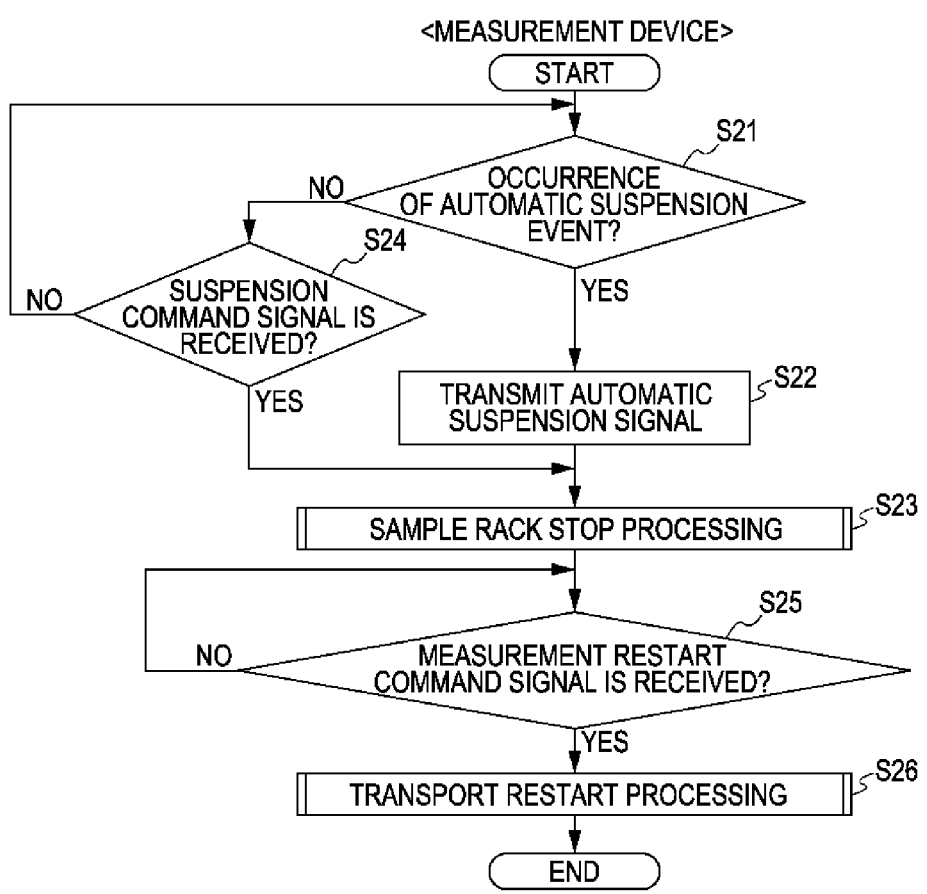

FIGS. 11A and 11B are flowcharts illustrating processing steps of a transport suspension and restart processing carried out by the measurement device 2 and the information processing device 3.

In the present embodiment, when the operator presses the measurement suspending button 441 illustrated in FIG. 9 to transmit the suspension command signal from the information processing device 3 to the measurement device 2, the transport operation of the sample rack is suspended. Having detected the occurrence of a predetermined transport automatic suspension event, more specifically, cuvette shortage detected by the cuvette storage quantity detector 234, filled-up waste solution tank detected by the liquid quantity detector 233, washing solution shortage detected by the liquid quantity detector 233, reagent shortage detected by the reagent residual quantity detector 232, or rack placement region C filled with sample racks L detected by the sensor C2 of the rack detector 235, the transport operation of the sample rack is suspended.

Referring to FIG. 11A, when the CPU 301 of the information processing device 3 receives a signal indicating the detection of any of the transport automatic suspension events (automatic suspension signal) from the measurement device 2 (S11: YES), the CPU 301 makes the display unit 320 of the information processing device 3 display thereon that the measuring operation was suspended (S14). When the operator presses the measurement suspending button 441 (S12: YES), the CPU 301 of the information processing device 3 transmits a suspension command signal to the measurement device 2 (S13). Then, the CPU 301 makes the display unit 320 of the information processing device 3 display thereon that the measurement was suspended (S14).

Figure 12:
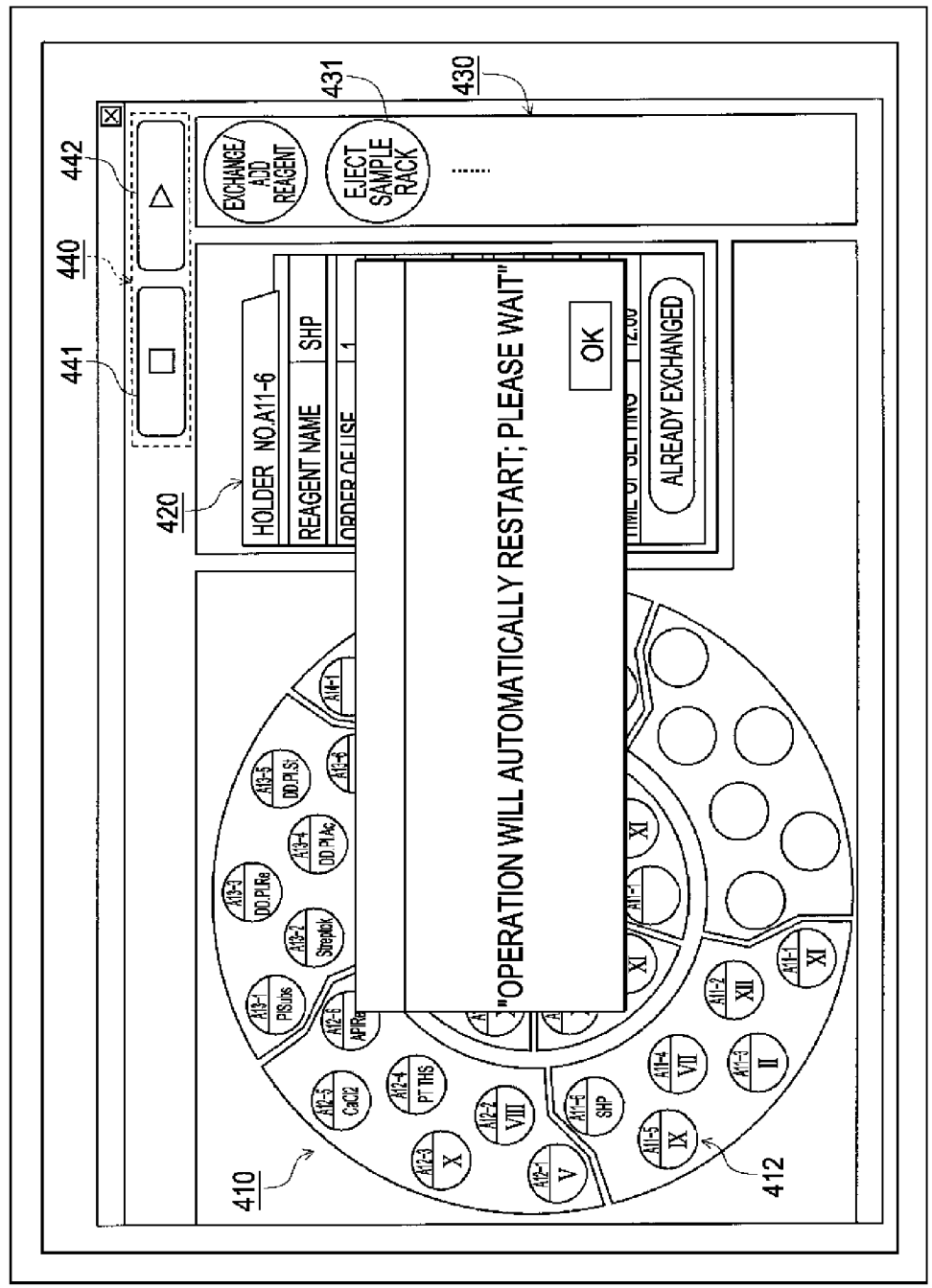
FIG. 12 is an illustration of a measurement suspension message displayed on the display unit of the information processing device according to the embodiment.

FIG. 12 is a diagram illustrating an example of the measurement suspension message displayed on the display unit 320 of the information processing device 3; wherein "the operation will automatically restart; please wait" is displayed. The message to be displayed may be "it is unnecessary to transport the sample rack; the transport of the sample rack will automatically start again when the measurement restarts". The operator can accordingly know it is unnecessary to reset the sample rack L in the rack set region A.

Referring to FIG. 11B, when the CPU 201 of the measurement device 2 detects any of the transport automatic suspension events (S21: YES), the CPU 201 transmits the automatic suspension signal to the information processing device 3 (S22), and stops the sample rack L by executing a "sample rack stop processing" (S23). When the CPU 201 of the measurement device 2 receives the suspension command signal from the information processing device 3 (S24: YES), the CPU 201 stops the sample rack L by executing a "sample rack stop processing" (S23). The "sample rack stop processing" will be described later with reference to FIG. 16.

Referring to FIG. 11A, when the operator commands to restart the measuring operation by the measurement device 2 via the information processing device 3 (S15: YES), the CPU 301 of the information processing device 3 transmits a measurement restart command signal to the measurement device 2 (S16), and ends the processing.

Referring to FIG. 11B, when the CPU 201 of the measurement device 2 receives the measurement restart command signal from the information processing device 3 (S25: YES), the CPU 201 restarts the transport operation of the sample rack L by executing a "transport restart processing" (S26), and then ends the processing steps. The "transport restart processing" will be described later with reference to FIG. 17.

In the case where the sample rack L is possibly positionally shifted during the time when the transport operation of the sample rack L temporarily stops and then restarts, it may be determined during this period of time whether or not the sample rack L is positionally shifted.

Figure 13:
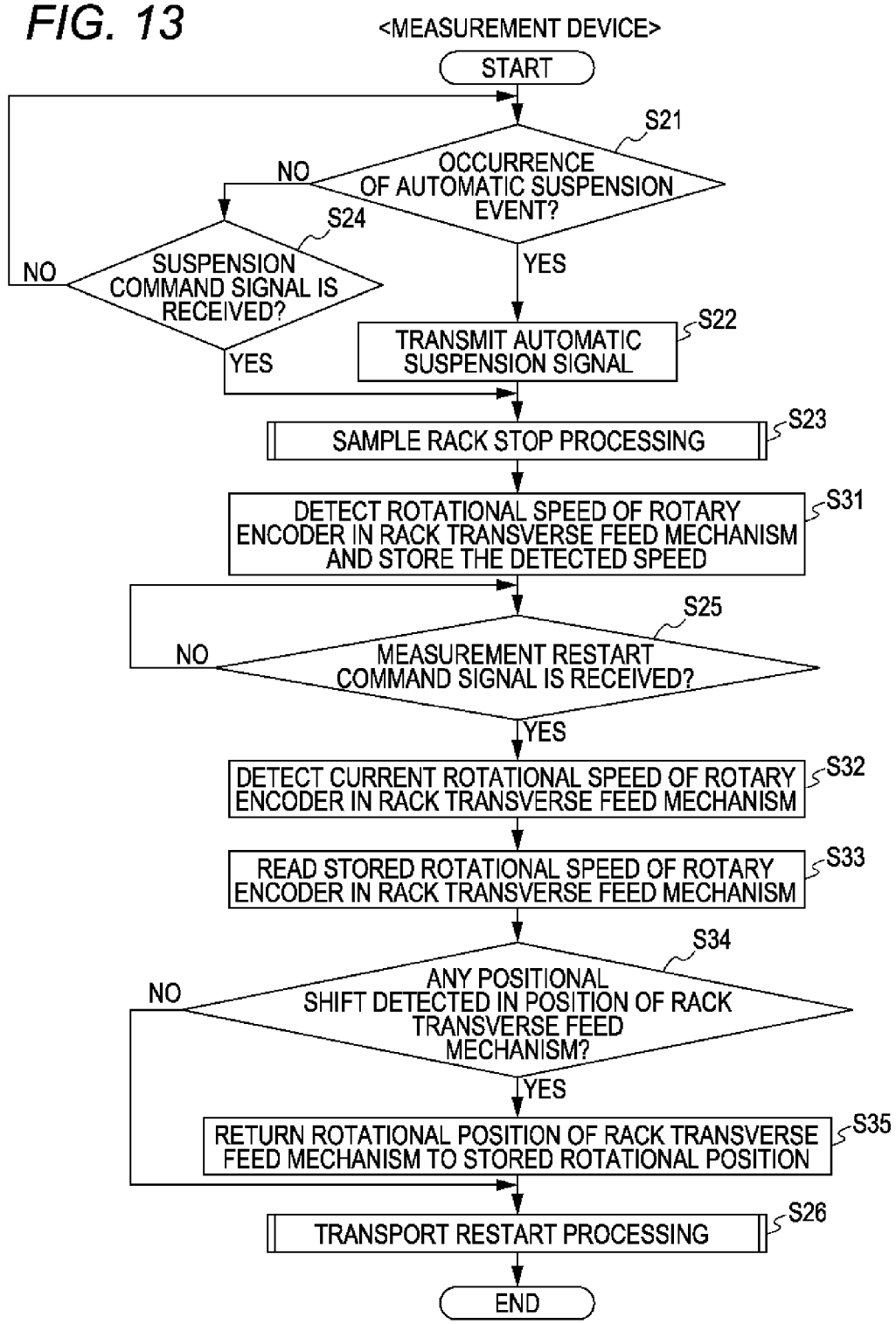
FIG. 13 is a modified example of a flowchart illustrating the suspension and restart processing according to the embodiment.

FIG. 13 is a modified flowchart illustrating processing steps of suspending and restarting the transport of the sample rack L by the CPU 201 of the measurement device 2. Only the processing steps which are different to the flow of the processing steps illustrated in FIG. 11A are described below.

In S31, the position of the sample rack L on the transport region B stopped by the "sample rack stop processing" is stored. More specifically, the rotational speed detected from the rotary encoder B44 of the rack transverse feed mechanism B2 which transports the sample rack L is stored in the RAM 303 or the hard disc 304 of the information processing device 3.

When the measurement restart is commanded (S25: YES), the current rotational speed of the rotary encoder B44 of the rack transverse feed mechanism B2 is detected (S32), and the rotational speed stored in S31 is read out (S33). When these two rotational speeds are compared to each other and determined that the rack transverse feed mechanism B2 is positionally shifted (S34: YES), the rack transverse feed mechanism B2 is returned to its position based on the rotational speed stored in S31 (S35).

Accordingly, in the case where the rack transverse feed mechanism B2 is positionally shifted immediately after the sample rack L was stopped, the rack transverse feed mechanism B2 can be returned to its proper position before the "transport restart processing" restarts the transport operation of the sample rack L. As a result, the transport operation of the sample rack L can smoothly restart.

FIG. 14A and FIG. 14B respectively illustrate a transport operation control list of a preceding rack and a transport operation control list of a subsequent rack. Of the two sample racks L currently transported in the transport region B, the sample rack L disposed downstream (X-axis positive direction) is the preceding rack, and the sample rack L disposed upstream (X-axis negative direction) is the subsequent rack.

The transport operation control list includes items of, for example, rack position, holding position, sample barcode read state, measurement mode, and suctioning state as illustrated in FIGS. 14A and 14B. The transport operation control list is stored in the RAM 203 or hard disc 204 of the measurement device 2. According to the transport operation control list, the transport operation of the pre-read sample rack L is controlled.

The item of "measurement mode" in the transport operation control list is obtained from a job list described later based on information of the barcode label BL2 of the sample rack L pre-read at the pre-read position. The job list retains therein measurement order information including respective sample measurement modes, measurement state information, and measurement results. The job list is updated when the sample container T newly measured is registered in the job list (hereinafter, referred to as "order-register"), when the measurement starts, and when the measurement result is obtained. As illustrated in FIG. 15, the measurement mode stored in the job list is linked to the rack number and the holding position of the sample container T (rack number—position). When the barcode label BL2 of the sample rack L is read at the pre-read position, the measurement mode linked to the holding position relevant to the rack number corresponding to the read barcode label BL2 is transcribed from the job list in the item of "measurement mode" of the subsequent rack. The item of "suctioning state" in the transport operation control list is updated from "unfinished" to "finished" when the sample is suctioned in S6 of FIG. 10.

Referring to FIG. 14A, it is known from the item of "rack position" that the preceding rack is at the sample suctioning position 52. It is known from the item of "sample barcode read state" that the pre-read by the barcode reader 51 has already been done for all of the holding positions. It is known from the item of "measurement mode" that standard measurement is performed for the sample containers T at the holding positions 1 to 4 and 7 to 10, and trace-level measurement is performed for the sample containers T at the holding positions 5 and 6. It is known from the item of "suctioning state" that the sample suctioning is already finished for the sample containers T at the holding positions 1 to 5, but the sample suctioning is still unfinished for the sample containers T at the holding positions 6 to 10.

Referring to FIG. 14B, it is known from the item of "rack position" that the subsequent rack is positioned at the pre-read position. It is known from the item of "sample barcode read state" that the pre-read by the barcode reader 51 has already been finished for the holding positions 1 to 5, but the pre-read by the barcode reader 51 is still unfinished for the holding positions 6 to 10. It is known from the item of "measurement mode" that standard measurement is performed for the sample containers T at the holding positions 1 to 3, 6 and 9 in the subsequent rack, and trace-level measurement is performed for the sample containers T at the retaining positions 4, 5, 7, 8 and 10 in the subsequent rack. It is known from the item of "suctioning state" that the sample suctioning is finished for none of the retaining positions.

When the preceding rack is transported to the rack placement region C and the subsequent rack at the pre-read position is positioned at the sample suctioning position 52 or 53, the transport operation control list of the preceding rack is overwritten with the transport operation control list of the subsequent rack, and the transport operation control list of the subsequent rack is initialized. When the next sample rack L is positioned at the pre-read position, the transport operation control list for the sample rack L subsequent thereto is created.

FIG. 15 is a diagram illustrating the job list.

As illustrated in the figure, the job list retains therein information such as measurement state, measurement order information, and measurement result of the sample container T which was order-registered. The job list is stored in the hard disc 304 of the information processing apparatus 3.

The job list includes items of, for example, state, rack number—position, sample number, measurement mode, date, time, and PT % (measurement result). The sample measurement state is written in the item of "state". For the sample just order-registered but not yet measured, the item of "state" shows "pending". When the sample rack L is ejected as described later, the item shows "error". When the sample measurement is terminated, the item of "state" becomes blank. The item of "rack number—position" shows a number affixed to the sample rack L for discrimination and a holding position of the sample container T. Each of the rack numbers is linked to information of the barcode label BL2 of the sample rack L. The item of "sample number" shows a number affixed to the sample container T for discrimination. Each of the "sample numbers" is linked to information of the barcode label BL1 of the sample container T. The items of "date" and "time" show a date and a time point when the sample is fetched into the measurement device 2. When the measuring operation is normally terminated, its measurement result is written in the item of "PT %". In the case where the measuring operation is not normally terminated, "***.*" (mask) is written in the item of "PT %". "PT %" is an example of possible measurement items, and the job list includes other measurement items.

Figure 16:
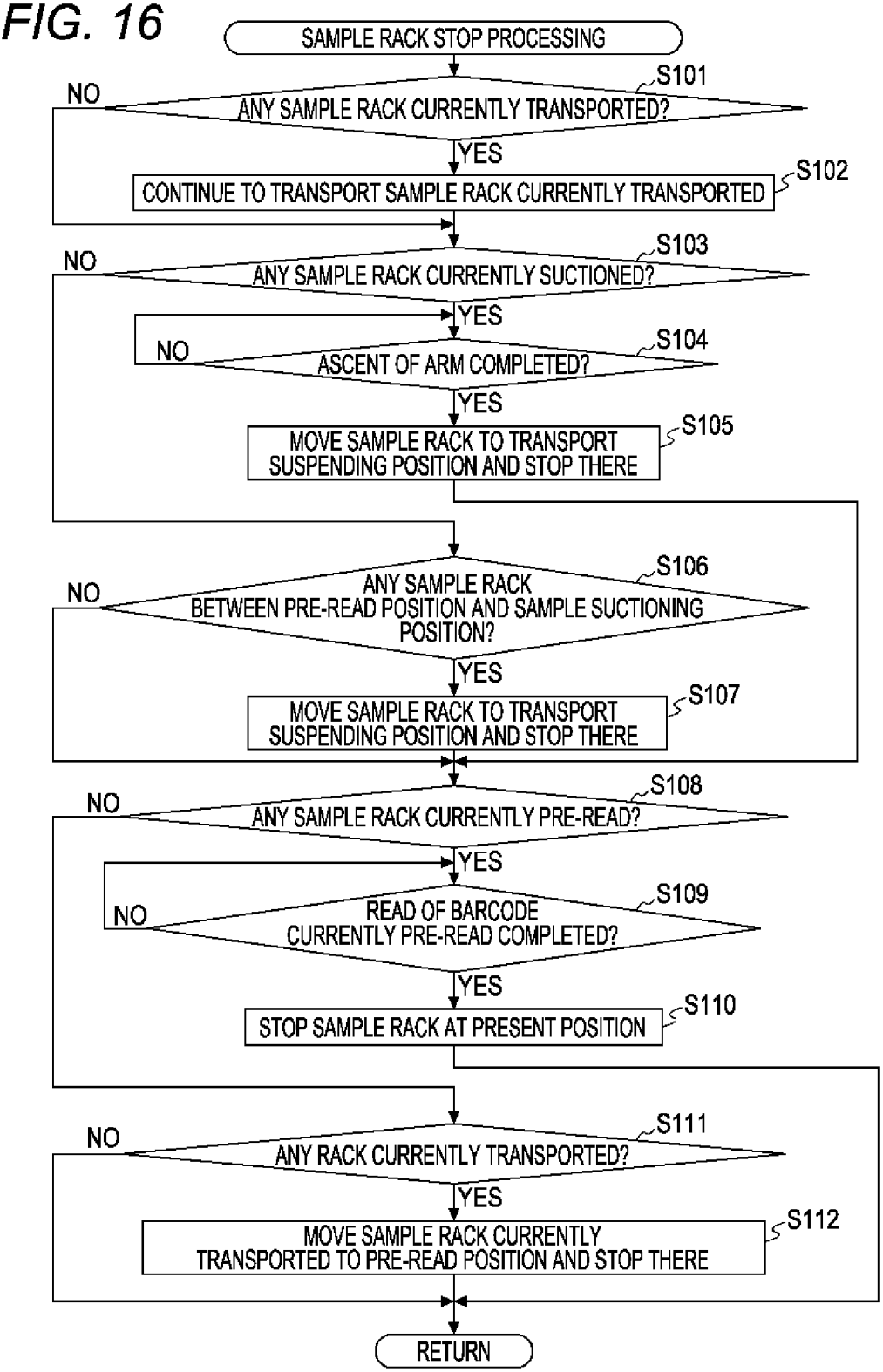
FIG. 16 is a flowchart illustrating a sample rack stop processing according to the embodiment.

FIG. 16 is a flowchart illustrating processing steps of the "sample rack stop processing" in the suspension and restart processing illustrated in FIG. 11 B.

At the time of occurrence of a transport suspension event, when the samples in all of the sample containers T in one sample rack L have been suctioned and there is another sample rack L currently transported to the rack placement region C (S101: YES), the sample rack L is transported to the rack placement region C (S102).

When the sample of any sample rack L is currently suctioned at the sample suctioning position 52 or 53 (S103: YES), the arm of the sample dispensing unit 21 or 22 is ascended. When the ascent of the arm of the sample dispensing unit 21 or 22 is completed (S104: YES), the sample rack L is transported to the transport suspending position illustrated in FIG. 4 to stop there (S105). The sensor B55 detects that the sample rack L was transported to the transport suspending position.

In the presence of any sample rack L between the pre-read position and the sample suctioning position 52 or 53 (S106: YES) while there is no sample rack L currently subject to the sample suctioning at the sample suctioning position 52 or 53, (S103: NO), the sample rack L is transported to the transport suspending position to stop there (S107). Thus, the sample rack L already pre-read and currently transported to the sample suctioning position 52 or 53 is positioned at the transport suspending position.

In the presence of the sample rack L currently pre-read at the pre-read position (S108: YES), the sample rack L stays at the pre-read position until the currently ongoing pre-read of the barcode of the sample container T or sample rack L is finished. After the read of the barcode of the sample container T or the sample rack L currently pre-read is finished (S109: YES), the sample rack L stops at the position (S110).

In presence of the sample rack L currently transported by the rack feed mechanism A1 in the rack set region A or the sample rack L currently transported to the pre-read position in the transport region B (S111: YES) while there is no sample rack L currently pre-read at the pre-read position (S108: NO), the sample rack L is transported to the pre-read position to stop there (S112). The sensor B52 detects that the sample rack L has been transported to the pre-read position. Then, the "sample rack stop processing" ends.

By the time when the transport operation restarts after the sample rack L is stopped in S105, S107, S110, and S112, the engagement claws B32a of the rack transverse feed mechanisms B2 illustrated in FIG. 5 remain engaged with the sample rack L. During such stoppage period, the stepping motor B43 is continuously excited so that the sample rack L can be prevented from positionally shifting. Accordingly, the transport operation of the sample rack L can restart without any trouble.

Figure 17:
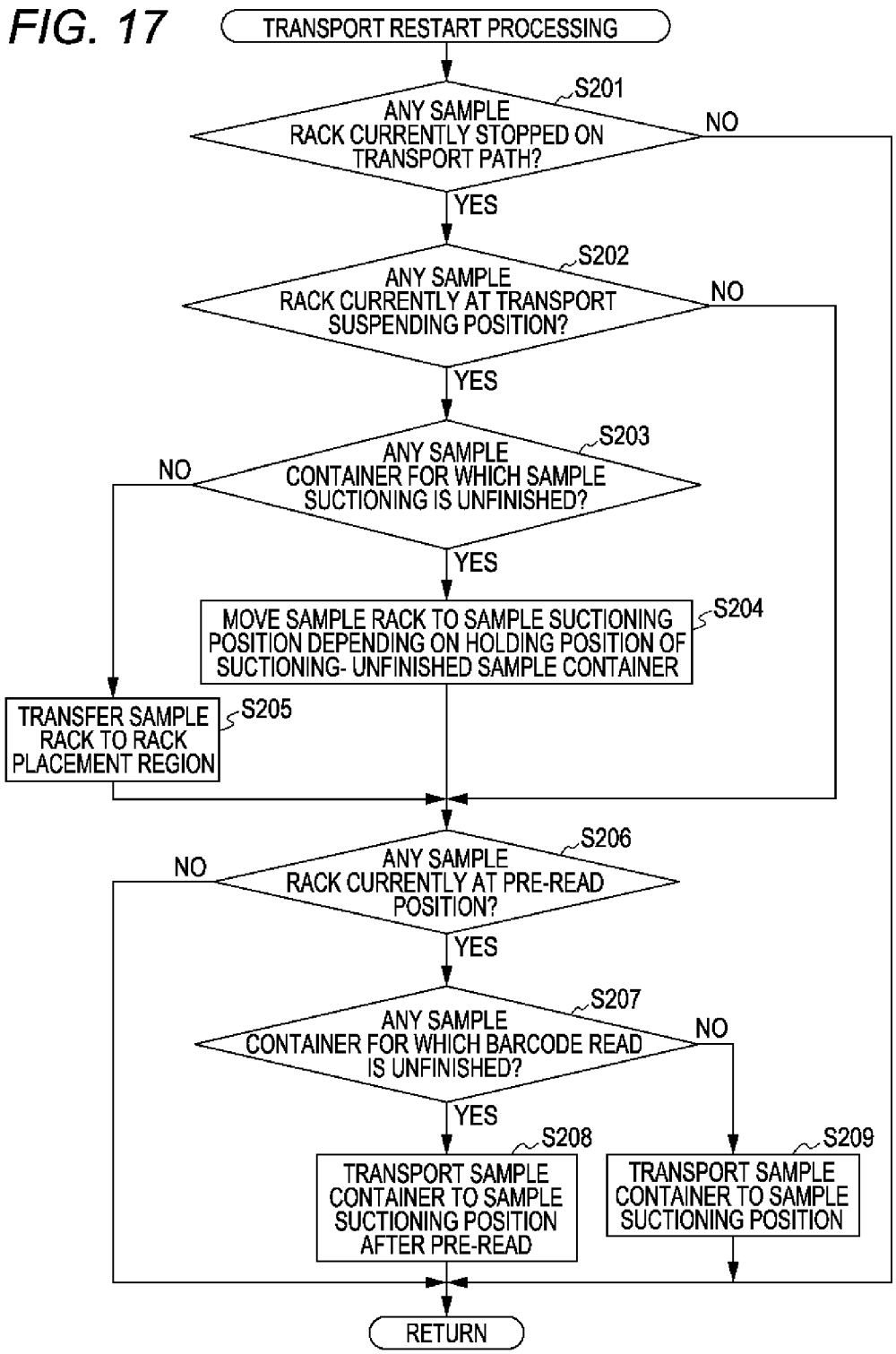
FIG. 17 is a flowchart illustrating a transport restart processing according to the embodiment.

FIG. 17 is a flowchart illustrating processing steps of the "transport restart processing" in the suspension and restart processing illustrated in FIG. 11.

In S201, it is determined whether there is any sample rack L currently stopped on the transport path B1 of the transport region B. In the presence of the sample rack L currently stopped on the transport path B1 (S201: YES), it is determined whether the sample rack L is at the transport suspending position (S202). In the absence of the sample rack L currently stopped on the transport path B1 (S201: NO), the processing steps end.

When determined that the sample rack L is at the transport suspending position (S202: YES), it is then determined whether or not the sample rack L has any sample containers T for which the sample suctioning is unfinished (S203). When determined that the sample rack L is not at the transport suspending position (S202: NO), a processing step of S206 is carried out.

When determined that the sample rack L has the sample container T for which the sample suctioning is unfinished (S203: YES), the transport operation control list is referred, and the sample rack L is transported to the sample suctioning position 52 or 53 depending on whether the sample in the suctioning-unfinished sample container T is subject to standard measurement or trace-level measurement according to the holding position thereof (S204). When there is no sample container T for which the sample suctioning is unfinished in the sample rack L (S203: NO), the sample rack L is transported to the rack placement region C (S205). In this manner, S204 selectively suctions only the sample container T for which the sample suctioning is unfinished, while skipping the sample container T from which the sample has been suctioned.

In the presence of any sample rack L at the pre-read position (S206: YES), it is determined whether there is any sample container T for which the barcode read by the barcode reader 51 is unfinished (S207). When there is no sample rack L at the pre-read position (S206: NO), the processing steps end.

In the presence of the sample container T for which the barcode read by the barcode reader 51 is unfinished (S207: YES), the barcode of the read-unfinished sample container T is read referring to the transport operation control list. In the case where the barcode read for any sample rack L is unfinished, the barcode of the sample rack L is similarly read. After the barcode read is finished, the sample rack L is transported to the sample suctioning position 52 or 53 (S208). When there is no sample container T for which the barcode read by the barcode reader 51 is unfinished (S207: NO), the sample rack L is transported to the sample suctioning position 52 or 53 (S209). In this manner, S208 reads only the read-unfinished barcode label, while skipping the already read barcode label. Then, the "transport restart processing" ends.

FIG. 18A is a flowchart illustrating processing steps for ejecting the sample rack L carried out by the measurement device 2 and the information processing device 3.

In the present embodiment, when the operator presses the ejection button 431 illustrated in FIG. 9 to transmit an ejection command signal from the information processing apparatus 3 to the measurement device 2, the sample rack currently transported is ejected into the rack placement region C. The sample rack L currently transported is similarly ejected into the rack placement region C when the occurrence of any of the following predetermined automatic ejection events is detected, that is, when operational abnormality of the sample dispensing units 21 and 22 and reagent dispensing units 23 to 25 is detected, when pressure supply abnormality in the pneumatic source of the drive unit 237 of the measurement unit is detected, when operational abnormality of the tables (reagent tables 11 and 12, cuvette table 15, and warming table 16) is detected, when the main body cover 29 left open is detected by the sensor unit 236, and when temperature abnormality of the warming table 16 is detected by the temperature detector 231.

Referring to FIG. 18A, when the CPU 301 of the information processing device 3 receives a signal indicating the detection of any of the automatic ejection events (automatic ejection signal) from the measurement device 2 (S41: YES), the CPU 301 makes the display unit 320 of the information processing device 3 display thereon information indicating the ejection of the sample rack L (S44). When the operator presses the sample rack ejection button 431 (S42: YES), the CPU 301 of the information processing device 3 transmits an ejection command signal to the measurement device 2 (S43). Then, the CPU 301 makes the display device 320 of the information display device 3 display thereon information indicating the ejection of the sample rack L (S44), and ends the processing steps.

Figure 18B:
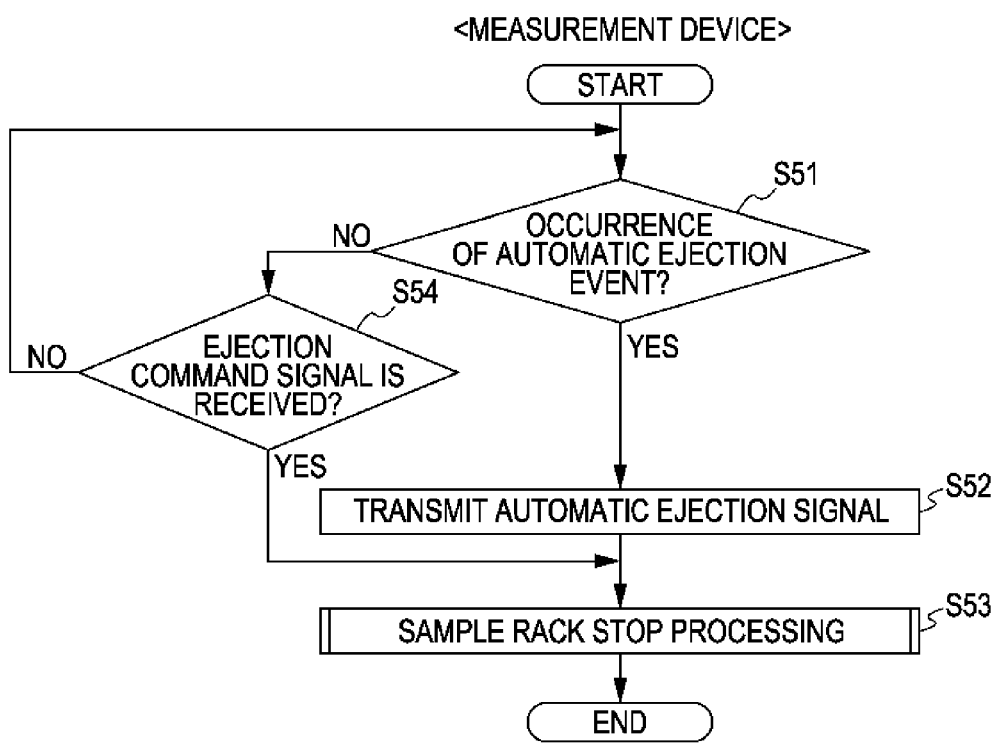

Referring to FIG. 18B, when the CPU 201 of the measurement device 2 detects any of the automatic ejection events (S51: YES), the CPU 201 transmits the automatic ejection signal to the information processing device 3 (S52), and ejects the sample rack L by executing a "sample rack ejection processing" (S53). When the CPU 201 of the measurement device 2 receives the ejection command signal from the information processing device 3 (S54: YES), the CPU 201 ejects the sample rack L by executing the "sample rack ejection processing" (S52). The "sample rack ejection processing" will be described with reference to FIG. 19.

FIG. 19 is a flowchart illustrating processing steps of the "sample rack ejection processing" in the ejection processing illustrated in FIG. 18A.

In S301, it is determined whether there is any sample rack L currently transported from the transport region B to the rack placement region C after the sample suctioning for their sample containers T is completed. When determined that such a sample rack L is present (S301: YES), the sample rack L is transported to the rack placement region C (S302). When determined that such a sample rack L is not present (S301: NO), the processing proceeds to S303.

In S303, it is determined whether there is any sample rack L whose sample is currently suctioned at the sample suctioning position 52 or 53. When determined that such a sample rack L is present (S303: YES), the arm of the sample dispensing unit 21 or 22 is ascended (S304). When the ascent of the arm of the sample dispensing unit 21 or 22 is completed (S304: YES), the sample rack L whose sample was suctioned is transported leftward (X-axis positive direction) along the transport region B to the rack placement region C (S305). When determined that no sample rack L whose sample is currently suctioned (S303: NO), the processing proceeds to S306.

In S306, it is determined whether there is any sample rack L positioned between the pre-read position and the sample suctioning position 52 or 53 after the pre-read is over. When determined that such a sample rack L is present (S306: YES), the sample rack L is transported leftward (X-axis positive direction) along the transport region B to the rack placement region C (S307). When determined that there is no sample rack between the pre-read position and the sample suctioning position 52 or 53 (S306: NO), the processing proceeds to S308.

In S308, it is determined whether there is any sample rack L currently pre-read. When determined that there is the sample rack L currently pre-read (S308: YES), the sample rack currently pre-read is transported leftward along the transport region B to the rack placement region C before the pre-read is over (S309). When determined that there is no sample rack L currently pre-read (S308: NO), the processing proceeds to S310.

In S310, it is determined whether there is any sample rack L currently transported on the transport region B toward the pre-read position. When determined that there is such a sample rack L (S310: YES), the sample rack L is immediately transported to the rack placement region C without the barcode read and sample suctioning (S311). When determined that there is no such a sample rack L (S310: NO), the processing proceeds to S312. By the time when the transport operation of the sample rack L starts toward the pre-read position after the sample rack L is transported from the rack set region A to the right end of the transport region B, it is determined as YES in S310.

In S312, it is determined whether there is any sample rack L currently transported on the rack set region A toward the right end of the transport region B. When determined that there is such a sample rack (S312: YES), the sample rack L is stopped at the position (S313), and the "sample rack ejection processing" ends. When determined that there is no such a sample rack L (S312: NO), the "sample rack ejection processing" ends.

The item of "state" of the job list illustrated in FIG. 15 currently showing "pending" is rendered blank for the sample container T whose sample was suctioned in all of the sample containers T retained in the sample rack L forcibly ejected by the processing described above. The item of "state" of the job list illustrated in FIG. 15 shows "error", and "mask" is written in the item of measurement result for the sample container T which was pre-read but forcibly ejected before its sample was suctioned.

Figure 18C:
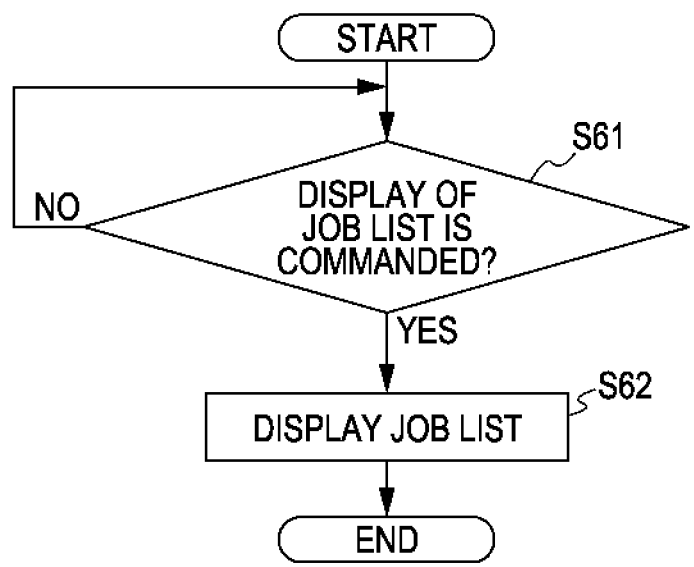
FIG. 18C is a flowchart illustrating a job list display processing according to the embodiment.

FIG. 18C is a flowchart illustrating processing steps of a job list display processing.

When the operator commands to display the job list via the information processing device 3 (S61: YES), a screen showing the job list is displayed on the display unit 320 of the information processing device 3 (S62).

According to the present embodiment, when the transport operation of the sample rack L is suspended, the transport of the sample rack L is stopped by the "sample rack stop processing" illustrated in FIG. 16. Then, the "transport restart processing" illustrated in FIG. 17 is executed to restart the transport operation of the sample rack L. Therefore, the operator does not have to return the sample rack L that stopped on the transport path to its initial position (rack set region A) when the transport operation of the sample rack L is suspended. Thus, the transport operation of the sample rack L can restart with less burden on the operator.

According to the present embodiment, the engagement claws B32a of the rack transverse feed mechanisms B2 are engaged with the recess La of the sample rack L during the suspension of the transport operation. Therefore, the sample rack L can be prevented from being displaced from the transport path B during the suspension of the transport operation. The stepping motor B43 is continuously excited during the suspension of the transport operation, which prevents the sample rack L from positionally shifting. As a result, the transport operation of the sample rack L can restart without any trouble.

When the position of the sample rack L is adjusted to return to the position when the transport was stopped before the transport operation restarts as illustrated in FIG. 13, the transport of the sample rack can smoothly restart regardless of any change generated in the position of the sample rack L due to some factor during the suspension of the transport operation.

According to the present embodiment, the sample rack L can be positioned in the area covered with the front cover 55 when the transport operation is suspended. Therefore, the operator can be prevented from accidentally coming into contact with the sample rack L during the suspension of the transport operation.

According to the present embodiment, the sample rack L is moved to the predetermined position (transport suspending position or pre-read position) and then stops there when any of the transport suspension events occurs, and the transport operation of the sample rack L restarts at the predetermined position. Accordingly, such a complicated control of the apparatus that the sample rack L is once returned to its initial position (rack set region A) before the transport operation restarts can be eliminated. As a result, the transport operation can more readily restart.

According to the present embodiment, the pipette of the sample dispensing unit 21, 22 is removed from the sample container T when the transport operation is suspended during the sample suctioning, and the sample rack L is then transported to the transport suspending position. Accordingly, any contact possibly made by the pipette of the sample dispensing unit 21, 22 with the sample container T and the sample rack L can be avoided when the sample rack L is transported to the transport suspending position.

According to the present embodiment, after the transport operation restarts, the sample is suctioned from the sample container T for which the sample suctioning is unfinished, while the sample container T whose sample is already suctioned is skipped based on the suctioning state of the transport operation control list. The transport operation can restart with an improved efficiency.

According to the present embodiment, after the transport operation restarts, the pre-read is performed for only the sample container T which has not been pre-read, while the pre-read is skipped for the sample container T already preread, based on the transport operation control list. Therefore, the sample rack L can be more speedily transported to the sample suctioning position 52, 53.

The embodiment of the present invention has been described so far. The present invention, however, is not necessarily limited to the embodiment, and the embodiment can be variously modified.

According to the above embodiment, the sample rack L is transported to the predetermined position (transport suspending position or pre-read position) and is then stopped when any of the transport suspension events occurs. However, the present invention is not limited thereto. The sample rack L may be stopped at its position when the transport suspension event occurs. For example, when the sample rack L is stopped at a position between the transport suspending position and the pre-read position when the transport suspension event occurs, the sample rack L may be stopped at this position. In this case, the sample rack L may be temporarily moved to the transport suspending position or the pre-read position that can be accurately grasped by the sensor to restart the transport operation of the sample rack L from this position. Accordingly, the transport operation of the sample rack L can restart in a more simplified control operation.

According to the above embodiment, the transport operation of the sample rack L restarts when the operator commands to restart the measuring operation. However, the present invention is not limited thereto. The transport operation of the sample rack L may automatically restart as soon as it is detected that the transport automatic suspension event (for example, cuvette shortage, reagent shortage) no longer exists.

According to the above embodiment, the sample processing apparatus 1 is a blood coagulation analyzing apparatus, however, the present invention is not limited thereto. Other examples of the sample processing apparatus 1 include: immunoassay apparatus for measuring blood serums, a hemocyte counting apparatus for counting hemocytes in whole blood, a urine analyzing apparatus for measuring urine, and an analyzing apparatus for analyzing bone marrow fluid.

According to the above embodiment, the measurement unit 10 which measures a sample is used as the sample processing unit. The sample processing unit may be a smear sample production unit for producing a smear sample by smearing a sample on a glass slide.

According to the above embodiment, during the suspension of the transport operation of the sample rack L, the engagement claws B32a of the rack transverse feed mechanisms B2 are engaged with the sample rack L as illustrated in FIG. 5C and FIG. 5D, and the stepping motor B43 is continuously excited to prevent any positional shift of the sample rack L. In replacement thereto, there may be additionally provided a lock mechanism for securing the sample rack L in a predetermined area of the transport region B when the transport of the sample rack L is suspended.

According to the above embodiment, the sample is suctioned from the sample container T positioned at the sample suctioning position 52 or 53 of the transport region B. However, the present invention is not limited thereto. The sample container T may be fetched into the measurement unit 10 from the sample rack L on the transport region B to suction the sample from the sample container T fetched into the measurement unit 10.

The embodiment of the present can be variously modified within the scope of the technical idea disclosed in the appended claims.

What is claimed is:

1. A sample processing apparatus, comprising:
   a sample processing unit for obtaining a sample from a sample container positioned at a sample obtaining position and performing a predetermined process of the sample;
   a transport unit for transporting a sample rack holding one or more sample containers through a transport path via the sample obtaining position from a first position at which sample rack enters the transport path to a second position at which the sample rack exits the transport path, the transport unit being configured to perform a transportation of the sample containers in the sample rack to the sample obtaining position;
   a detector for detecting a residual quantity of at least one of a reagent, cuvettes, and a washing solution a used by the sample processing unit; and
   a transport controller configured to:
   suspend the transportation process of the transport unit to cause the sample rack to wait in a transport suspending position between the first and second positions until receiving a restart instruction when the detector detects that the residual quantity is less than a predetermined residual quantity during the transportation process, and restart the transportation process of the transport unit to transport the sample rack from the transport suspending position to the sample obtaining position without returning to the first position when the restart instruction is received.

2. The sample processing apparatus of claim 1, wherein the transport unit comprises an engagement mechanism driven to engage with the sample rack, and an engagement driver for driving the engagement mechanism; and
the transport controller controls the engagement driver to keep the engagement mechanism engaged with the sample rack until the transport controller restarts the transport operation.

3. The sample processing apparatus of claim 2, wherein the engagement mechanism comprises engagement claws configured to extend and retract, wherein the sample rack comprises a recess that engages with the engagement claws only when the claws are extended, and wherein the claws are extended only between the transport suspension event and the restart of the transport operation.

4. The sample processing apparatus of claim 2, wherein
the transport unit comprises a movement mechanism for moving the engagement mechanism engaged with the sample rack in a direction where the sample rack is transported, a motor for actuating the movement mechanism, and a motor driving circuit for driving the motor; and
the transport controller continuously causes the motor to excite by the driving section while the engagement mechanism is kept engaged with the sample rack until the transport controller restarts the transport operation.

5. The sample processing apparatus of claim 1, wherein
the transport unit comprises a cover portion for covering a part of a transport path of the sample rack; and
the predetermined position is a position covered with the cover portion.

6. The sample processing apparatus of claim 1, wherein
the sample processing unit comprises a pipette for suctioning the sample from the sample container held by the sample rack;
the transport controller controls the transport unit to transport the sample rack to the predetermined position after the pipette is removed from the sample container, if the detector detects that the residual quantity is less than the predetermined residual quantity while the pipette was inserted in the sample container.

7. The sample processing apparatus of claim 1, wherein
the transport unit comprises a rack receiving section for receiving the sample rack that exits the transport path; and
the transport controller controls the transport unit to transport the sample rack to the rack receiving section without causing the sample rack to wait at the transport suspending position, if the detector detects that the residual quantity is less than the predetermined residual quantity after all of the samples have been obtained from the sample containers held by the sample rack.

8. The sample processing apparatus of claim 1, wherein
the sample processing apparatus further comprises a memory for storing information indicating a respective sample obtaining state for each of the sample containers held by the sample rack; and
the transport controller restarts the transportation based on the sample obtaining state stored in the memory.

9. The sample processing apparatus of claim 8, wherein
the transport controller controls the transport unit, to restart the transportation, so that a given one of the sample containers, from which a sample has not been obtained, is positioned at the sample obtaining position, and a further one of the sample containers, from which a sample has been obtained is transported to a position other than the sample obtaining position, if the detector detects that the residual quantity is less than the predetermined residual quantity while a sample container held by the sample rack was positioned at the sample obtaining position.

10. The sample processing apparatus of claim 1, wherein
the sample processing apparatus further comprises an identification information reader for reading respective identification information for each of the sample containers held by the sample rack before the sample rack is transported to the sample obtaining position; and
when the detector detects that the residual quantity less than the predetermined residual quantity after the reading of the identification information is completed for all of the sample container held by the sample rack and before the transportation begins, the transport controller controls the transport unit to cause the sample rack to wait in the transport suspending position until receiving a restart instruction, and to start the transportation without returning the sample rack to a position where the identification information is read by the identification information reader when the restart instruction received.

11. The sample processing apparatus of claim 10, wherein
the transport controller controls the transport unit to transport the sample rack to the sample obtaining position after the reading of the identification information has been completed for all of the sample containers held by the sample rack, if the reading of the identification information was not completed for a part of the sample containers held by the sample rack when the detector detects that the residual quantity is less than the predetermined residual quantity.

12. The sample processing apparatus of claim 1, wherein
the transport controller obtains restart position information indicating a position where the sample rack is positioned when the transport operation of the sample rack restarts, and controls the transport unit to restart the transportation based on the restart position information.

13. The sample processing apparatus of claim 1, further comprising
a display for showing a notification that the transport unit will automatically restart the transportation when the transportation by the transport unit has been suspended.

14. The sample processing apparatus of claim 1, wherein
the transport suspending position is a position where a part of the sample rack is overlapped with the sample obtaining position.

15. The sample processing apparatus of claim 1, wherein
the transport path is a path on which the sample rack is transported in a first direction from the first position to the second position and in a second direction that is a reverse direction of the first direction,
the transport controller determines one of the first and second directions for transporting the sample container that contains a sample to be obtained next to the sample obtaining position from the transport suspending position and a distance to transport, and controls the transport unit to transport the sample rack at the transport suspending position in the determined direction and distance.

16. The sample processing apparatus of claim 1, wherein the sample obtaining position is a sample suctioning position of a first sample dispensing unit in a standard measurement or a sample suctioning of a second sample dispensing unit in a trace-level measurement.

17. A sample rack transporting method comprising:
- transporting a sample rack holding one or more sample containers through a transport path via a sample obtaining position from a first position at which the sample rack enters the transport path to a second position at which the sample rack exits the transport path, so that the sample containers in the sample rack are positioned at the sample obtaining position;
- obtaining, by a sample processing unit, a sample from the sample container positioned at the sample obtaining position on the transport path and performing a predetermined process of the obtained sample;
- causing the sample rack to wait in a transport suspending position between the first position and the second position when detecting that a residual quantity of at least one of a reagent, cuvettes and a washing solution used by the sample processing unit is less than a predetermined residual quantity during the transportation of the sample rack; and
- restarting the transportation of the sample rack by transporting the sample rack from the transport suspending position to the sample obtaining position so that the sample container that contains the sample to be obtained next is transported to the sample obtaining position without retuning to the first position when a shortage of the reagent, cuvettes or the washing solution is solved.

* * * * *